(12) United States Patent
Schumacher et al.

(10) Patent No.: US 10,881,836 B2
(45) Date of Patent: Jan. 5, 2021

(54) SHEATH ASSEMBLY FOR INSERTION OF A CORD-SHAPED ELEMENT, PARTICULARLY A CATHETER, INTO THE BODY OF A PATIENT

(71) Applicant: ECP ENTWICKLUNGSGESELLSCHAFT MBH, Berlin (DE)

(72) Inventors: Joerg Schumacher, Teltow (DE); Lars Bredenbreuker, Berlin (DE); Robert Decke, Berlin (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 35 days.

(21) Appl. No.: 16/122,517

(22) Filed: Sep. 5, 2018

(65) Prior Publication Data

US 2019/0105471 A1 Apr. 11, 2019

Related U.S. Application Data

(63) Continuation of application No. 14/654,078, filed as application No. PCT/EP2013/077798 on Dec. 20, 2013, now Pat. No. 10,080,871.

(Continued)

(30) Foreign Application Priority Data

Dec. 21, 2012 (EP) ..................................... 12199220

(51) Int. Cl.
*A61M 25/00* (2006.01)
*A61M 25/06* (2006.01)
(Continued)

(52) U.S. Cl.
CPC ...... *A61M 25/0662* (2013.01); *A61M 1/1008* (2014.02); *A61M 25/0111* (2013.01);
(Continued)

(58) Field of Classification Search
CPC .. A61M 2025/0004; A61M 2025/0681; A61M 2039/0633; A61M 25/0662; A61M 39/0613; A61M 39/1011
See application file for complete search history.

(56) References Cited

U.S. PATENT DOCUMENTS

| 2,350,534 A | 6/1944 | Rosinger |
| 3,333,127 A | 7/1967 | Congdon et al. |

(Continued)

FOREIGN PATENT DOCUMENTS

| CA | 2613175 A1 | 1/2007 |
| CA | 2632420 A1 | 6/2007 |

(Continued)

OTHER PUBLICATIONS

Brochure Impella Pumpsystem of Impella CardioSystems AG, "Turning Lives Around," Aug. 2003 (4 pages).

(Continued)

*Primary Examiner* — Deanna K Hall
(74) *Attorney, Agent, or Firm* — Botos Churchill IP Law LLP

(57) ABSTRACT

Sheath assembly for the insertion of a cord-shaped element (32, 105), comprising an introducer sheath (101) and an auxiliary sheath (104) for insertion into the introducer sheath (101) together with the cord-shaped element (32, 105), with first fastening means (106) for detachably fastening the auxiliary sheath to the introducer sheath, and with second fastening means (107) for detachably fastening the cord-shaped element to the auxiliary sheath, wherein the introducer sheath (101) has a first sheath housing (13, 114) and (Continued)

Figure 1:
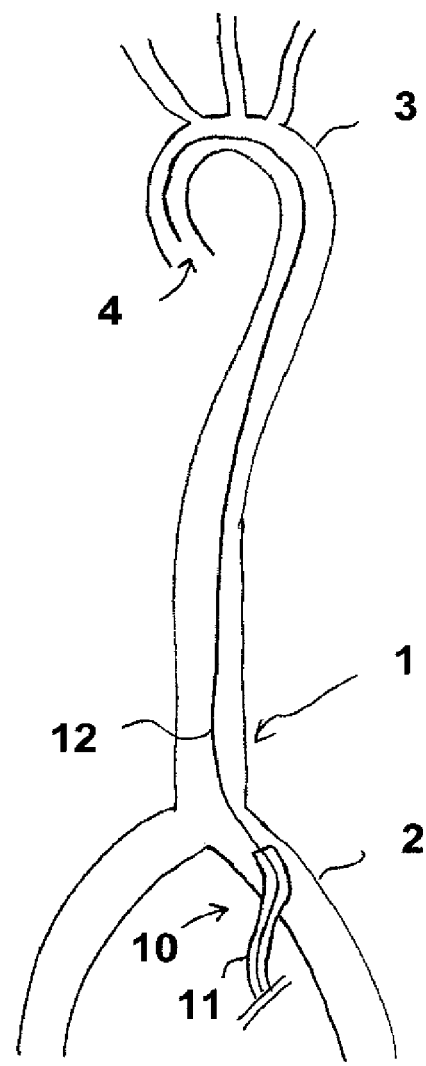

a distal tubular section (11, 41 *a*) that terminates in the first sheath housing, and a first flushing device (108), wherein the auxiliary sheath (104) has a second sheath inner chamber (111), a distal, tubular part (112) and a second flushing device (109).

10 Claims, 14 Drawing Sheets

Related U.S. Application Data

(60) Provisional application No. 61/740,597, filed on Dec. 21, 2012.

(51) Int. Cl.
    *A61M 39/10*     (2006.01)
    *A61M 39/06*     (2006.01)
    *A61M 1/10*      (2006.01)
    *A61M 25/01*     (2006.01)
    *A61M 1/12*      (2006.01)

(52) U.S. Cl.
CPC .... *A61M 39/0613* (2013.01); *A61M 39/1011* (2013.01); *A61M 1/101* (2013.01); *A61M 1/1034* (2014.02); *A61M 1/122* (2014.02); *A61M 1/125* (2014.02); *A61M 25/0097* (2013.01); *A61M 25/0668* (2013.01); *A61M 2025/0004* (2013.01); *A61M 2025/0006* (2013.01); *A61M 2025/0019* (2013.01); *A61M 2025/0675* (2013.01); *A61M 2025/0681* (2013.01); *A61M 2039/062* (2013.01); *A61M 2039/0673* (2013.01); *A61M 2205/32* (2013.01)

(56) References Cited

U.S. PATENT DOCUMENTS

| | | |
|---|---|---|
| 3,354,833 A | 11/1967 | Laing |
| 3,489,145 A | 1/1970 | Judson et al. |
| 3,936,683 A | 2/1976 | Walker |
| 4,065,234 A | 12/1977 | Yoshiyuki et al. |
| 4,115,040 A | 9/1978 | Knorr |
| 4,135,253 A | 1/1979 | Reich et al. |
| 4,153,048 A | 5/1979 | Magrini |
| 4,420,851 A | 12/1983 | Wiener |
| 4,610,674 A | 9/1986 | Suzuki et al. |
| 4,679,558 A | 7/1987 | Kensey et al. |
| 4,686,982 A | 8/1987 | Nash |
| 4,699,611 A | 10/1987 | Bowden |
| 4,728,319 A | 3/1988 | Masch |
| 4,747,821 A | 5/1988 | Kensey et al. |
| 4,747,840 A | 5/1988 | Ladika et al. |
| 4,749,376 A | 6/1988 | Kensey et al. |
| 4,753,221 A | 6/1988 | Kensey et al. |
| 4,777,951 A | 10/1988 | Cribier et al. |
| 4,846,152 A | 7/1989 | Wampler et al. |
| 4,895,557 A | 1/1990 | Moise et al. |
| 4,919,647 A | 4/1990 | Nash |
| 4,984,972 A | 1/1991 | Clausen et al. |
| 5,011,469 A | 4/1991 | Buckberg et al. |
| 5,017,103 A | 5/1991 | Dahl |
| 5,037,403 A | 8/1991 | Garcia |
| 5,042,984 A | 8/1991 | Kensey et al. |
| 5,061,256 A | 10/1991 | Wampler |
| 5,097,849 A | 3/1992 | Kensey et al. |
| 5,139,486 A | 8/1992 | Moss |
| 5,147,186 A | 9/1992 | Buckholtz |
| 5,158,279 A | 10/1992 | Laffey et al. |
| 5,163,431 A | 11/1992 | Griep |
| 5,167,636 A | 12/1992 | Clement |
| 5,169,378 A | 12/1992 | Figuera |
| 5,234,425 A | 8/1993 | Fogarty et al. |
| 5,250,059 A | 10/1993 | Andreas et al. |
| 5,275,580 A | 1/1994 | Yamazaki |
| 5,282,790 A | 2/1994 | Clement |
| 5,304,142 A | 4/1994 | Liebl et al. |
| 5,320,611 A | 6/1994 | Bonutti et al. |
| 5,357,963 A | 10/1994 | Mayol et al. |
| 5,376,114 A | 12/1994 | Jarvik |
| 5,395,341 A | 3/1995 | Slater |
| 5,397,310 A | 3/1995 | Chu et al. |
| 5,405,383 A | 4/1995 | Barr |
| 5,407,430 A | 4/1995 | Peters |
| 5,421,338 A | 6/1995 | Crowley et al. |
| 5,480,392 A | 1/1996 | Mous |
| 5,488,960 A | 2/1996 | Toner |
| 5,492,530 A | 2/1996 | Fischell et al. |
| 5,536,255 A | 7/1996 | Moss |
| 5,573,517 A | 11/1996 | Bonutti et al. |
| 5,653,697 A | 8/1997 | Quiachon et al. |
| 5,749,855 A | 5/1998 | Reitan |
| 5,827,171 A | 10/1998 | Dobak, III et al. |
| 5,863,179 A | 1/1999 | Westphal et al. |
| 5,888,241 A | 3/1999 | Jarvik |
| 5,911,702 A | 6/1999 | Romley et al. |
| 5,935,122 A | 8/1999 | Fourkas et al. |
| 5,938,672 A | 8/1999 | Nash |
| 5,954,745 A | 9/1999 | Gertler et al. |
| 5,971,993 A | 10/1999 | Hussein et al. |
| 5,984,944 A | 11/1999 | Forber |
| 6,001,078 A | 12/1999 | Reekers |
| 6,054,788 A | 4/2000 | Dombrovski et al. |
| 6,083,260 A | 7/2000 | Aboul-Hosn |
| 6,123,725 A | 9/2000 | Aboul-Hosn |
| 6,129,704 A | 10/2000 | Forman et al. |
| 6,183,220 B1 | 2/2001 | Ohara et al. |
| 6,197,016 B1 | 3/2001 | Fourkas et al. |
| 6,245,007 B1 | 6/2001 | Bedingham et al. |
| 6,338,730 B1 | 1/2002 | Bonutti et al. |
| 6,350,278 B1 | 2/2002 | Lenker et al. |
| 6,413,222 B1 | 7/2002 | Pantages et al. |
| 6,428,556 B1 | 8/2002 | Chin |
| 6,517,528 B1 | 2/2003 | Pantages et al. |
| 6,533,716 B1 | 3/2003 | Schmitz-Rode et al. |
| 6,537,247 B2 | 3/2003 | Shannon |
| 6,540,712 B1 | 4/2003 | Parodi et al. |
| 6,544,216 B1 | 4/2003 | Sammler et al. |
| 6,613,038 B2 | 9/2003 | Bonutti et al. |
| 6,656,153 B1 | 12/2003 | Sakai et al. |
| 6,692,462 B2 | 2/2004 | Mackenzie et al. |
| 6,814,715 B2 | 11/2004 | Bonutti et al. |
| 6,841,910 B2 | 1/2005 | Gery |
| 6,858,001 B1 | 2/2005 | Aboul-Hosn |
| 6,974,436 B1 | 12/2005 | Aboul-Hosn et al. |
| 6,976,996 B1 | 12/2005 | Aboul-Hosn |
| 6,981,942 B2 | 1/2006 | Khaw et al. |
| 7,022,100 B1 | 4/2006 | Aboul-Hosn et al. |
| 7,025,746 B2 | 4/2006 | Tal |
| 7,027,875 B2 | 4/2006 | Siess et al. |
| 7,166,088 B2 | 1/2007 | Heuser |
| 7,393,181 B2 | 7/2008 | McBride et al. |
| 7,632,254 B1 | 12/2009 | Bjorkman et al. |
| 7,646,376 B2 | 1/2010 | Blersch |
| 7,722,567 B2 | 5/2010 | Tal |
| 7,731,675 B2 | 6/2010 | Aboul-Hosn et al. |
| 7,841,976 B2 | 11/2010 | McBride et al. |
| 7,914,492 B2 | 3/2011 | Heuser |
| 7,927,068 B2 | 4/2011 | McBride et al. |
| 8,066,674 B2 | 11/2011 | Heuser |
| 8,079,948 B2 | 12/2011 | Shifflette |
| 8,439,859 B2 | 5/2013 | Pfeffer et al. |
| 8,597,277 B2 | 12/2013 | Lenker et al. |
| 8,672,888 B2 | 3/2014 | Tal |
| 8,758,402 B2 | 6/2014 | Jenson et al. |
| 8,888,728 B2 | 11/2014 | Aboul-Hosn et al. |
| 9,623,228 B2 | 4/2017 | Ryan et al. |
| 2001/0000528 A1 | 4/2001 | Cho |
| 2002/0120226 A1 | 8/2002 | Beck |
| 2002/0151799 A1 | 10/2002 | Pantages et al. |
| 2003/0135086 A1 | 7/2003 | Khaw et al. |

(56) References Cited

U.S. PATENT DOCUMENTS

| | | |
|---|---|---|
| 2003/0135940 A1 | 7/2003 | Lev et al. |
| 2003/0208097 A1 | 11/2003 | Aboul-Hosn et al. |
| 2004/0022640 A1 | 2/2004 | Siess et al. |
| 2004/0044266 A1 | 3/2004 | Siess et al. |
| 2004/0113502 A1 | 6/2004 | Li et al. |
| 2004/0147877 A1* | 7/2004 | Heuser .............. A61M 25/0662 604/165.02 |
| 2004/0193046 A1 | 9/2004 | Nash et al. |
| 2004/0230287 A1 | 11/2004 | Hartley et al. |
| 2004/0260237 A1 | 12/2004 | Squadrito |
| 2005/0135942 A1 | 6/2005 | Wood et al. |
| 2005/0149097 A1 | 7/2005 | Regnell et al. |
| 2005/0149105 A1 | 7/2005 | Leeflang et al. |
| 2005/0245892 A1 | 11/2005 | Elkins et al. |
| 2006/0008349 A1 | 1/2006 | Khaw |
| 2006/0062672 A1 | 3/2006 | McBride et al. |
| 2006/0135981 A1 | 6/2006 | Lenker et al. |
| 2006/0195004 A1 | 8/2006 | Jarvik |
| 2006/0287574 A1 | 12/2006 | Chin |
| 2007/0118072 A1 | 5/2007 | Nash |
| 2007/0299499 A1 | 12/2007 | Hartley et al. |
| 2008/0004569 A1 | 1/2008 | McCrystle et al. |
| 2008/0004571 A1 | 1/2008 | Voss |
| 2008/0033396 A1 | 2/2008 | Danek et al. |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0065011 A1 | 3/2008 | Marchand et al. |
| 2008/0082165 A1 | 4/2008 | Wilson et al. |
| 2008/0097386 A1 | 4/2008 | Osypka |
| 2008/0103591 A1 | 5/2008 | Siess |
| 2008/0114339 A1 | 5/2008 | McBride et al. |
| 2008/0132747 A1 | 6/2008 | Shifflette |
| 2008/0177249 A1 | 7/2008 | Heuser et al. |
| 2008/0183136 A1 | 7/2008 | Lenker et al. |
| 2008/0319387 A1 | 12/2008 | Amisar et al. |
| 2009/0012476 A1 | 1/2009 | Catlin |
| 2009/0024201 A1 | 1/2009 | Fitzgerald et al. |
| 2009/0060743 A1 | 3/2009 | McBride et al. |
| 2009/0062597 A1 | 3/2009 | Shifflette |
| 2009/0088609 A1 | 4/2009 | Schmitz-Rode et al. |
| 2009/0093764 A1 | 4/2009 | Pfeffer et al. |
| 2009/0093796 A1 | 4/2009 | Pfeffer et al. |
| 2009/0218728 A1 | 9/2009 | Moyer |
| 2009/0227892 A1 | 9/2009 | Krombach et al. |
| 2009/0240202 A1 | 9/2009 | Drasler et al. |
| 2010/0004730 A1 | 1/2010 | Benjamin et al. |
| 2010/0030161 A1 | 2/2010 | Duffy |
| 2010/0160863 A1 | 6/2010 | Heuser |
| 2010/0210895 A1 | 8/2010 | Aboul-Hosn et al. |
| 2010/0268017 A1 | 10/2010 | Siess |
| 2011/0071338 A1 | 3/2011 | McBride et al. |
| 2013/0035628 A1 | 2/2013 | Garrison et al. |
| 2013/0041202 A1 | 2/2013 | Toellner |
| 2013/0066140 A1 | 3/2013 | McBride et al. |
| 2013/0131718 A1 | 5/2013 | Jenson et al. |
| 2013/0197621 A1 | 8/2013 | Ryan et al. |
| 2013/0317438 A1 | 11/2013 | Ellingwood et al. |
| 2013/0317481 A1 | 11/2013 | Ellingwood et al. |
| 2014/0018732 A1 | 1/2014 | Bagaoisan et al. |
| 2015/0073202 A1 | 3/2015 | Aboul-Hosn et al. |
| 2016/0066948 A1 | 3/2016 | Ellingwood et al. |
| 2016/0220358 A1 | 8/2016 | Wilson et al. |
| 2016/0354583 A1 | 12/2016 | Ellingwood et al. |
| 2017/0056063 A1 | 3/2017 | Ellingwood et al. |
| 2017/0281908 A1 | 10/2017 | Ellingwood et al. |

FOREIGN PATENT DOCUMENTS

| | | |
|---|---|---|
| CA | 2701810 A1 | 4/2009 |
| DE | 4414903 A1 | 11/1995 |
| DE | 29804046 U1 | 4/1998 |
| DE | 10059714 C1 | 5/2002 |
| DE | 102005039950 A1 | 3/2007 |
| EP | 0364293 A2 | 4/1990 |
| EP | 0445782 A1 | 9/1991 |
| EP | 0768900 A1 | 4/1997 |
| EP | 0914171 A2 | 5/1999 |
| EP | 0916359 A1 | 5/1999 |
| EP | 1034808 A1 | 9/2000 |
| EP | 1207934 A2 | 5/2002 |
| EP | 2047872 A1 | 4/2009 |
| EP | 2229965 A1 | 9/2010 |
| EP | 2347778 A1 | 7/2011 |
| EP | 2 399 639 A1 | 12/2011 |
| FR | 2788223 A1 | 7/2000 |
| JP | H04126158 A | 4/1992 |
| JP | 2003503164 A | 1/2003 |
| JP | 2010537726 A | 12/2010 |
| JP | 2011526815 A | 10/2011 |
| WO | WO-9944651 A1 | 9/1999 |
| WO | WO-9958170 A1 | 11/1999 |
| WO | WO-2000019097 A1 | 4/2000 |
| WO | WO-2000043053 A1 | 7/2000 |
| WO | WO-2001083016 A2 | 11/2001 |
| WO | WO-2002022200 A1 | 3/2002 |
| WO | WO-2002043791 A1 | 6/2002 |
| WO | WO-2003103745 A2 | 12/2003 |
| WO | WO-2006020942 A1 | 2/2006 |
| WO | WO-2006034158 A2 | 3/2006 |
| WO | WO-2010063494 A1 | 6/2010 |
| WO | WO-2011089022 A1 | 7/2011 |
| WO | WO-2011/115048 A1 | 9/2011 |

OTHER PUBLICATIONS

Buecker A et al., "Use of a Nonmetallic Guide Wire for Magnetic Resonance—Guided Coronary Artery Catheterization," Investigative Radiology, 39:11, pp. 656-660 (2004).

Compendium of Technical and Scientific Information for the Hemopump Temporary Cardiac Assist System, 1988 (15 pages).

Dekker, Andre, et al, "Efficacy of a New Intraaortic Propeller Pump vs the Intraaortic Balloon Pump," Chest Journal; Jun. 2003 (7 pages).

Frazier, O.H., et al, "First Human Use of the Hemopump, A Cather-Mounted Ventricular Assist Device," Ann Thorac Surg., Feb.; 49(2): pp. 299-304 (1990).

International Preliminary Report on Patentability, from PCT/EP09/008858, dated Jun. 7, 2011.

JOMED Reitan Catheter Pump Brochure, www.jomed.com/rcp (undated) (6 pages).

Lueger, Lexikon der Technik, "Lexikon der Feinwerktechnik", vol. 13, Deutsche Verlags-Anstalt GmbH, Stuttgart, seite 551 (1968).

Reitan, Oyvind et al, "Hydrodynamic Properties of a New Percutaneous Intra-aortic Axial Flow Pump," ASAIO Journal; May-Jun.; vol. 16; pp. 323-329 (2000).

Rothman, Martin T, "The Reitan Catheter Pump: A New Versatile Approach for Hemodynamic Support," London Chest Hospital Barts & The Long NHS Trust, presented at TCT Conference, Oct. 24-26, 2006, (40 pages).

Schmitz-Rode, T et al, "Temporary Pulmonary Stent Placement as Emergency Treatment of Pulmonary Embolism," Journal of the American College of Cardiology, 48:4, pp. 812-816 (2006).

Schmitz-Rode, T et al., "An Expandable Percutaneous Catheter Pump for Left Ventricular Support," Journal of the American College of Cardiology, 45:11, pp. 1856-1861 (2005).

Siess, Thorsten, "Systemanalyse und Entwicklung intravasaler Rotationspumpen zur Herzunterstutzung," Helmholtz-Institut, Jun. 24, 1998 (105 pages) and partial English translation (37 pages).

Verma, R et al., "Evaluation of a Newly Developed Percutaneous Thrombectomy Basket Device in Sheep with Central Pulmonary Embolisms," Investigative Radiology, 41:10, pp. 729-734 (2006).

Wampler, Richard, K., "In Vivo Evaluation of a Peripheral Vascular Access Axial Flow Blood Pump," ASAIO Trans., Jul.-Sep.;34(3): pp. 450-454 (1988).

(56) References Cited

OTHER PUBLICATIONS

Office Action for corresponding Japanese Appl. No. 2018-088996 dated Mar. 3, 2020.

* cited by examiner

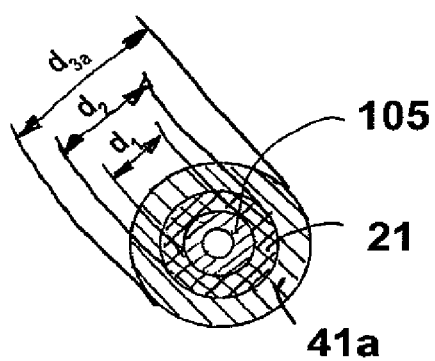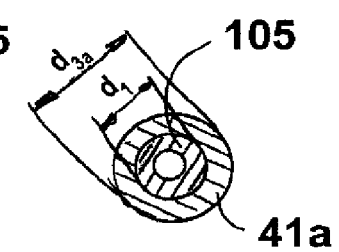
Fig. 19a  Fig. 19b  Fig. 19c

SHEATH ASSEMBLY FOR INSERTION OF A CORD-SHAPED ELEMENT, PARTICULARLY A CATHETER, INTO THE BODY OF A PATIENT

CROSS REFERENCE TO RELATED APPLICATIONS

This application is a continuation of U.S. application Ser. No. 14/654,078, filed Jun. 19, 2015, which is a national stage filing under 35 U.S.C. § 371 of International Application No. PCT/EP2013/077798, filed on Dec. 20, 2013, which claims priority to U.S. Provisional Application Ser. No. 61/740,597, filed Dec. 21, 2012, and to European Patent Application No. 12199220.0, filed Dec. 21, 2012. International Application No. PCT/EP2013/077798 was published under PCT Article 21(2) in English. The specifications of each of the foregoing applications are hereby incorporated by reference in their entirety.

The invention relates to the field of mechanics and can be used with particular advantage in the field of medical technology. More particularly, it relates to a sheath assembly which enables a cord-shaped element, particularly a catheter, to be inserted at least partially into the body of a patient.

It is known, in principle, to use an introducer sheath for the purpose of inserting a catheter into the body of a patient, for example, into a blood vessel, with the proximal end of said sheath protruding from the body of the patient while the distal end remains inside the body of the patient. Such introducer sheaths can be designed as integrated, for example, however they can also be simply inserted under sterile conditions through the skin or through an orifice in the body of the patient. Such a sheath is advantageous, for example, when a catheter will be inserted into a blood vessel of a patient and will also be removed therefrom. One particular application of such catheters involves catheters having functional elements, for example, hollow catheters at the end of which a blood pump is located, which will be transported through a blood vessel up to a chamber of the heart or up to a larger blood vessel, where it will optionally be expanded. Suitable blood pumps which can be expanded and later re-compressed are known in multiple forms in the literature.

However, other devices can also be attached to the catheter as functional elements, for example, surgical cutting devices for removing deposits in blood vessels or the like.

Particularly for the insertion of catheter pumps, it has already been proposed to use an auxiliary sheath in addition to an introducer sheath, with the catheter having the compressed pump being inserted into the auxiliary sheath, wherein the auxiliary sheath temporarily holds the end portion of the catheter and the compressed pump and is inserted together with the pump into the introducer sheath.

It is known to provide a flushing device inside a sheath, in the sheath inner chamber where an object will be inserted into the sheath, which device can be used to flush the element to be inserted and/or the sheath intake prior to insertion or during insertion in order to prevent bacteria and/or air from penetrating into the body of the patient. It is also known to provide sealing devices on sheaths of this type, in order, on one hand, to prevent blood or other bodily fluids from escaping from the sheath prior to insertion of an element through the sheath, and on the other hand, to seal the opening through which an element will be inserted into the sheath from the area outside said opening to the greatest possible extent during insertion of said element into the sheath.

In light of the described prior art, the object of the present invention is to devise a sheath assembly comprising an introducer sheath and an auxiliary sheath which will permit the insertion of a cord-shaped element, particularly a catheter, by means of the auxiliary sheath into the introducer sheath in the most comfortable manner possible, thereby generally preventing, to the greatest extent possible, bacteria or other undesirable objects and substances from penetrating into the body of the patient. The sheath assembly is also to be protected to the greatest possible extent against the escape of bodily fluids. Furthermore, trauma to the patient is to be minimized to the greatest possible extent, to which end the outer diameter of the introducer sheath is to exceed the outer diameter of the (optionally compressed) functional element and/or the catheter as little as possible.

The problem is solved by features specified in this application.

The solution involves a sheath assembly for the insertion of a cord-shaped element, particularly a catheter, into the body of a patient, comprising an introducer sheath, the distal end of which is provided for insertion into the body of a patient and the proximal end of which protrudes from the body of the patient when the distal end is inserted into the body of the patient, and comprising an auxiliary sheath for insertion into the introducer sheath together with the cord-shaped element/catheter, with first fastening means for particularly detachably fastening the auxiliary sheath to the introducer sheath, and with second fastening means for particularly detachably fastening the cord-shaped element to the auxiliary sheath, wherein the introducer sheath has a first sheath inner chamber having a first receiving channel for a cord-shaped element and a first flushing device for flushing the sheath inner chamber, wherein the auxiliary sheath has a second sheath inner chamber having a second receiving channel for a cord-shaped element and a second flushing device for the second sheath inner chamber. For example, the solution involves a sheath assembly for the insertion of a cord-shaped element, particularly a catheter, into the body of a patient, comprising an introducer sheath, the distal end of which is provided for insertion into the body of a patient, and the proximal end of which protrudes from the body of the patient when the distal end is inserted into the body of the patient, and comprising an auxiliary sheath for insertion into the introducer sheath together with the cord-shaped element/catheter, with first fastening means for particularly detachably fastening the auxiliary sheath to the introducer sheath, and with second fastening means for particularly detachably fastening the cord-shaped element to the auxiliary sheath, wherein the introducer sheath has a first sheath housing, and located therein, a first sheath inner chamber having a first receiving channel for a cord-shaped element and a distal, tubular section which terminates in the first sheath housing, and a first flushing device for flushing the sheath inner chamber, wherein the auxiliary sheath has a second sheath inner chamber having a second receiving channel for a cord-shaped element, a distal, tubular part and a second flushing device for the second sheath inner chamber, and wherein the first sheath housing has means for positioning the distal end of the tubular part of the auxiliary sheath in the first sheath housing and proximally in front of the proximal end of the tubular section.

The sheath assembly according to the invention ensures that the auxiliary sheath can be permanently and reliably attached to the introducer sheath, and that both the introducer sheath and the auxiliary sheath can thereby be flushed and thus kept clean and sterile. In the interior of the introducer sheath, the inner chamber between the auxiliary sheath and the introducer sheath and/or between the distal part of the auxiliary sheath and the introducer sheath can be flushed and thereby kept sterile. Inside the auxiliary sheath, the region inside the auxiliary sheath along with the cord-shaped element, particularly the catheter, that is located in or protrudes into said region can be flushed and thereby kept sterile. This results in an overall assembly which is permanently held together mechanically, at least until the connection between introducer sheath and auxiliary sheath is deliberately released, and which permits flushing in a simple manner at the transition from the introducer sheath to the auxiliary sheath and at the transition from the auxiliary sheath to the cord-shaped element located therein. In this manner, it can be ensured that, on one hand, the number of microbes and/or other contaminants that penetrate from the exterior into the introducer sheath is minimized, while at the same time blood is prevented from escaping from the introducer sheath and the auxiliary sheath.

The means for positioning the tubular part of the auxiliary sheath inside the introducer sheath can advantageously comprise a cylindrical channel inside the introducer sheath, the diameter of which corresponds to the diameter of the tubular part of the auxiliary sheath or does not deviate substantially from this diameter, that is, by no more than 30% and particularly by no more than 15%. An annular land, projecting radially inward, in the form of a narrowing of a channel for the tubular part of the auxiliary sheath, which land forms an axial stop or an axial stop of a different configuration, can also be provided. A corresponding land can leave a round opening, the diameter of which corresponds to the inner diameter of the tubular part of the auxiliary sheath or does not deviate substantially from this diameter, that is, by no more than 30% and particularly by no more than 15%. Such an axial stop can also be offset, and can therefore be located within the tubular section of the introducer sheath. It is possible to design the system such that the auxiliary sheath is inserted into the tubular section of the introducer sheath only far enough that the auxiliary sheath itself remains proximal to the opening in the patient's skin. This allows the diameter of the introducer sheath to exceed the diameter of the compressed functional element of the catheter only minimally, thereby minimizing the trauma and risk of bleeding to the patient.

In another further development, the inner diameter of the tubular section of the auxiliary sheath can also be greater than the inner diameter of the tubular section of the introducer sheath, as a result of which the functional element is compressed in two stages. First, in a first step, as the catheter is being advanced into the auxiliary sheath, the functional element is compressed to the inner diameter of the auxiliary sheath. As it is being transferred to the introducer sheath, the diameter of the functional element is then further compressed until it corresponds to the inner diameter of the introducer sheath. This two-stage compression ensures that the forces for compressing the functional element do not exceed a critical value at which the connection of the functional element to the catheter would be destroyed, for example. The same applies similarly to sheaths having a non-circular cross-section, for example, sheaths having an oval or elliptical cross-section.

One advantageous embodiment of the invention provides that the auxiliary sheath has a tubular distal part and a proximal sheath housing, and that only the tubular part is connected, particularly detachably, to the introducer sheath.

In this case, the tubular part of the auxiliary sheath can be clamped in a simple manner, and therefore detachably fastened, inside the introducer sheath, wherein an advantageous assembly is configured such that the difference in concentricity of the tubular sections of the sheaths in relation to one another in the clamping region is no greater than 30% of the larger inner sheath diameter, and particularly advantageously is no greater than the difference between the diameters of the sheaths. This helps to prevent the cord-shaped element/catheter from having to surmount edges created by the difference in diameters which might damage the cord-shaped element/catheter during the transfer thereof from the auxiliary sheath into the introducer sheath. Inside the auxiliary sheath, the exterior of the tubular part of the auxiliary sheath can be kept sterile by means of a flushing device, and the interior of the introducer sheath can be kept sterile by means of a flushing device. A cord-shaped element/catheter, for example with a compressed blood pump, can be contained inside the tubular part of the auxiliary sheath during insertion of this part into the introducer sheath. Once the tubular part of the auxiliary sheath has been inserted into the introducer sheath, the blood pump can be transferred from the auxiliary sheath into the introducer sheath, for example, into a tubular part of the introducer sheath. In this process, the sterility of the surrounding area is simultaneously ensured during the transfer process by flushing the interior of the introducer sheath.

A sterile tube, in which the tubular part of the auxiliary sheath can be arranged, can be attached, fluid-tight, to the end face of the introducer sheath. The sterile tube can terminate in a fluid-tight manner at the auxiliary sheath, particularly the housing thereof. The sterile tube can be axially compressible, to allow the auxiliary sheath, particularly the tubular part thereof, to be pushed into the introducer sheath and deposited there once the cord-shaped element has been inserted into the introducer sheath. The sterile tube can be embodied, for example, as a corrugated tube.

A further advantageous embodiment of the invention provides that the auxiliary sheath has a tubular, distal part and a sheath housing, and that the sheath housing of the auxiliary sheath is connected, particularly detachably, to the introducer sheath, particularly to a sheath housing of the introducer sheath.

If the sheath housing of the auxiliary sheath is fixedly connected to the sheath housing of the introducer sheath, this will result in a solid and non-deformable unit as a whole, which can be handled particularly easily on the body of the patient. It is then also particularly easy to insert the cord-shaped element through the auxiliary sheath into the introducer sheath. Once the auxiliary sheath has been connected to the introducer sheath, the sheath assembly acts as a single, multistage sheath.

The invention can further be advantageously embodied in that the auxiliary sheath is connected to the introducer sheath in the form of a detachable, force-sheathing or friction-sheathing clamp connection, a double-cone connection, a screw connection, a bayonet connection, a press-fit connection or some other detachable mated connection. Detachable connections of this type can be easily produced and then released again under surgical conditions. Due to the simple mechanical functioning, no chemically active joining agents are required, and therefore, there is no risk of contamination when used in live patients. The relevant connection can be released just as easily as it is produced.

Individual examples of corresponding detachable connections will be specified in greater detail further below in connection with the embodiment examples.

The invention can further be advantageously implemented in that the second flushing device is connected to the first flushing device. In this case, it is provided, in particular, that fluid can be exchanged between the first and second flushing devices, so that the same fluid is used for both flushing devices. This decreases cost and increases the certainty of sterility. The same pump may also be used for the first and second flushing devices for moving the flushing fluid, for example.

In this case, it can advantageously be provided that the inner chamber of the sheath housing of the auxiliary sheath is connected directly to the first flushing device by means of an auxiliary flushing channel. In one implementation, for example, the auxiliary flushing channel can extend through a line in the form of a hose or tube, which is attached to the outer periphery of the housing of the auxiliary sheath. In this case, the flushing device of the auxiliary sheath and the flushing device of the introducer sheath can have the same design, in which only the two flushing channels are connected to one another.

However, it can also be advantageously provided that the auxiliary flushing channel extends directly from the sheath housing of the introducer sheath into the interior of the tubular part of the auxiliary sheath, particularly through openings in the outer surface of the tubular part of the auxiliary sheath. Therefore, within the inner chamber of the sheath housing of the introducer sheath, the interior of the auxiliary sheath, particularly the interior of a tubular part of the auxiliary sheath, can be flushed along with the exterior region of the auxiliary sheath located inside the introducer sheath in that the tubular part of the auxiliary sheath has openings in the outer surface thereof, through which the flushing fluid can penetrate. The flushing fluid can then advantageously flow in an axial direction along the tubular part of the auxiliary sheath, allowing the auxiliary sheath to be flushed as a whole unit.

In this case, the flushing fluid is able to travel from the introducer sheath into the sheath housing of the auxiliary sheath, and is thereby able to move, in principle, between the auxiliary sheath and the cord-shaped element/catheter located therein, so that the catheter/cord-shaped element as such is also kept sterile. Said catheter/cord-shaped element will be inserted into the body of the patient, and therefore, the cord-shaped body itself/the catheter must be kept sterile.

A further advantageous embodiment of the invention provides that, in the case of a direct connection between the sheath housing of the auxiliary sheath and the sheath housing of the introducer sheath, the auxiliary flushing channel extends within the connecting region, particularly through a region of the wall of the sheath housing of the auxiliary sheath that is located within the introducer sheath, or also through a part of the wall of the housing of the introducer sheath that is encompassed by part of the auxiliary sheath. In this embodiment, a fixed, channel-like connection between the inner chamber of the introducer sheath and the inner chamber of the housing of the auxiliary sheath is produced, which allows the flushing fluid to be reliably transferred between the inner chambers of the housings of the two sheaths. In addition, at least one opening in the outer surface of the housing of the auxiliary sheath can be provided, which can serve either for discharging the flushing fluid or for venting.

Alternatively or additionally, a hypodermic needle can also be attached to the distal end of the auxiliary sheath, for example, penetrating through a rubber gasket, for example, a dome gasket or plate gasket, in the introducer sheath as the auxiliary sheath is being inserted into the introducer sheath, and projecting into the interior of the flushing chamber of the introducer sheath. As a result of this, a communication channel is produced by the hollow chamber of the needle between the inner chamber of the housing of the introducer sheath and the housing of the auxiliary sheath.

One advantageous embodiment of the invention further provides that the introducer sheath and the auxiliary sheath abut one another in an annular region as connecting partners, and that in the annular region, an annular or arcuate circumferential groove, extending in the circumferential direction, is provided in at least one of the two connecting partners, and that in both the sheath housing of the introducer sheath and the sheath housing of the auxiliary sheath, a channel-like recess is provided, which connects the interior of the respective sheath to the circumferential groove in the connected state. In this case, either a housing part of the introducer sheath can encompass a housing part of the auxiliary sheath in the connection region, or conversely, a housing part of the auxiliary sheath can encompass a housing part of the introducer sheath in said region.

Because the channel-like recesses in the housing, particularly in the housing wall, of the introducer sheath and in the housing, particularly the housing wall, of the auxiliary sheath are connected to one another by means of an annular or arcuate channel, even a rotation of the auxiliary sheath relative to the introducer sheath will not prevent the establishment of the connection between the channel-like recesses. This results in high reliability in establishing the connection between the flushing chambers of the introducer sheath and the auxiliary sheath as soon as the two housings are connected to one another, regardless of any rotation of the parts relative to one another. In this connection, the channel-like recesses and/or the circumferential channel can be configured such that at least the channel provided in the housing of the introducer sheath, and particularly both channels, are closed by a sliding element as soon as the two sheath housings are separated from one another.

In what follows, the invention will be specified in reference to an embodiment example illustrated in a set of drawings, and will be described in greater detail below. First, possible methods for securing an auxiliary sheath in an introducer sheath or a catheter in an auxiliary sheath will be described, after which the combination of flushing devices and the fastening of the two sheaths to one another will be specified in greater detail.

Figure 2:
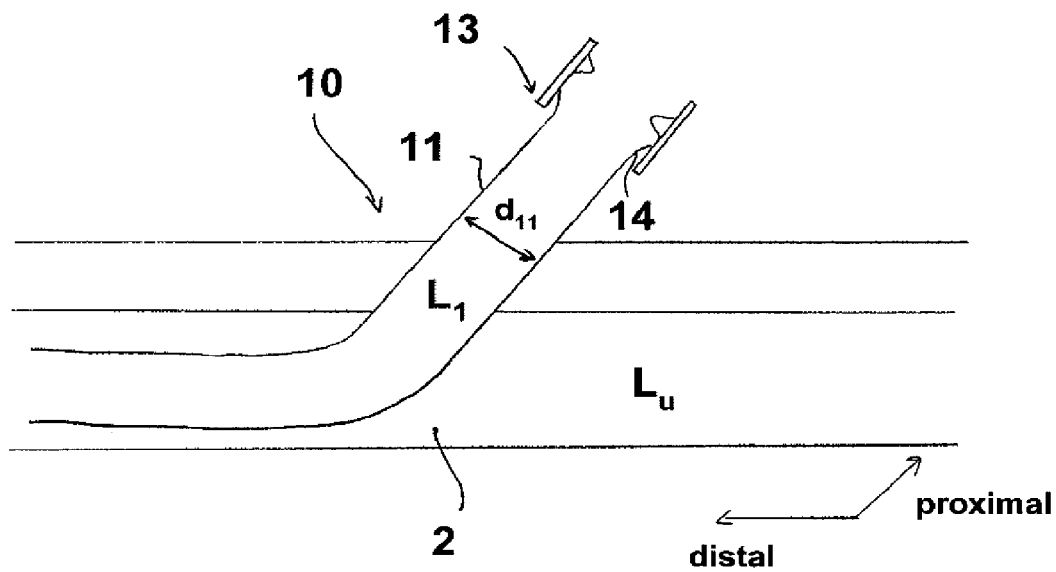
Figure 3:
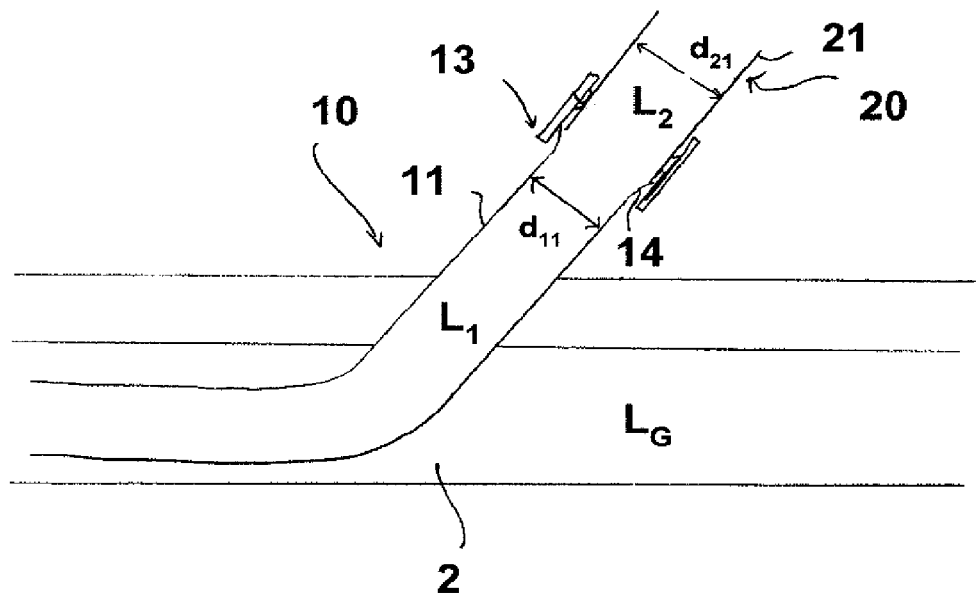
Figure 4:
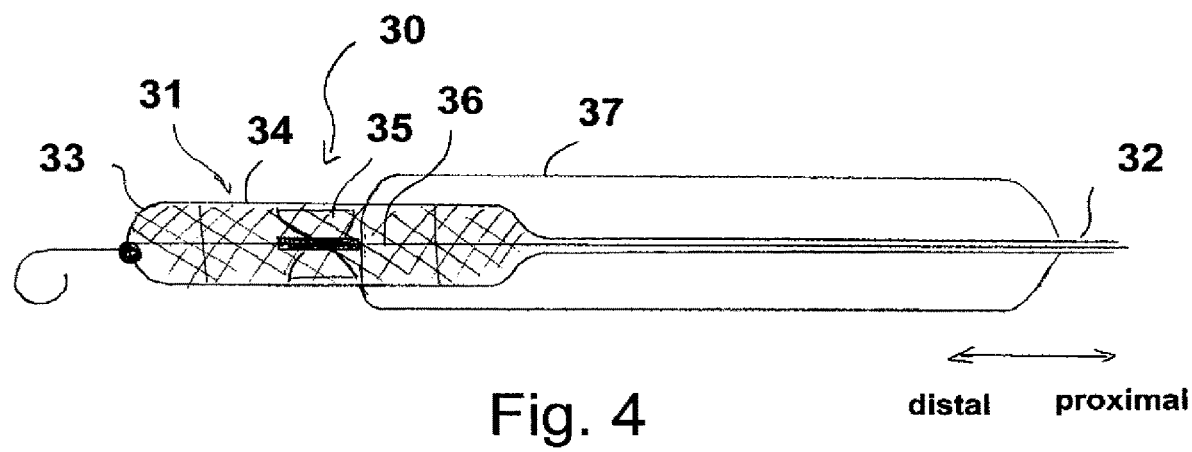
Figure 5:
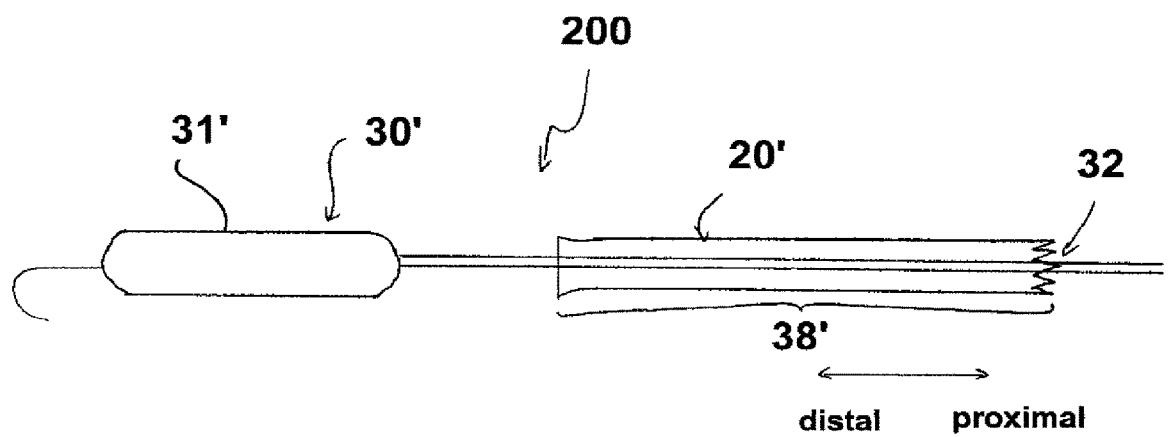
Figure 6:
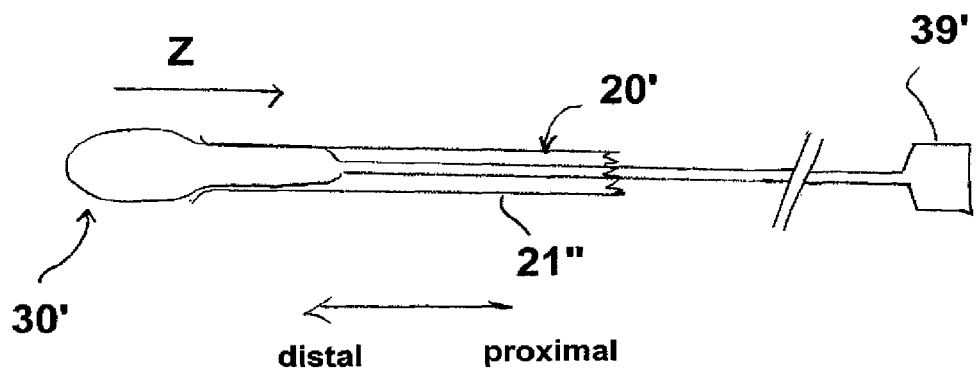
Figure 7:
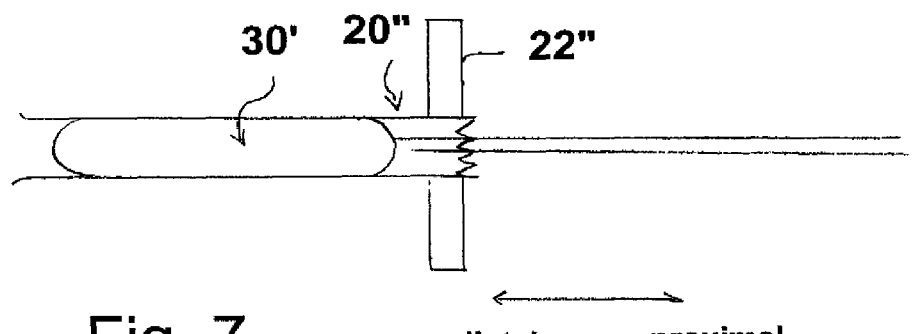
Figure 8:
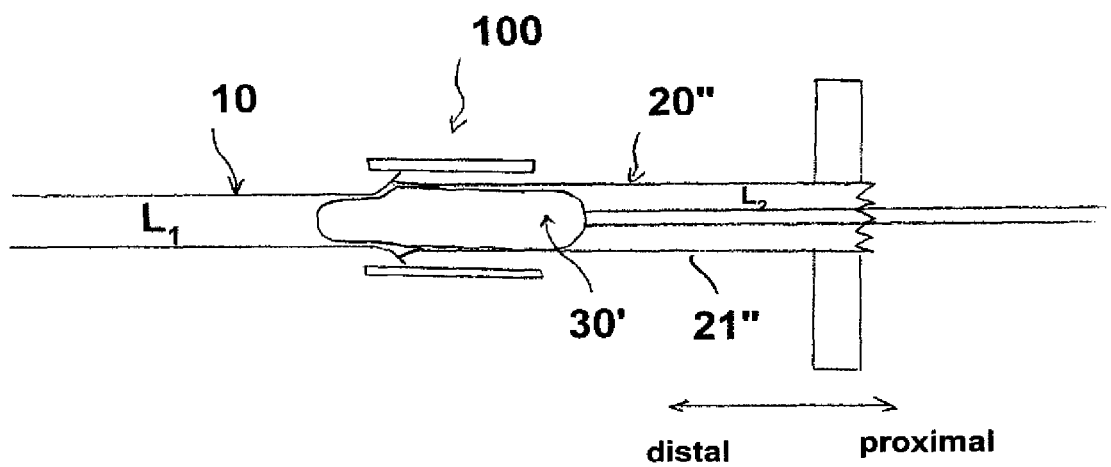
Figure 9:
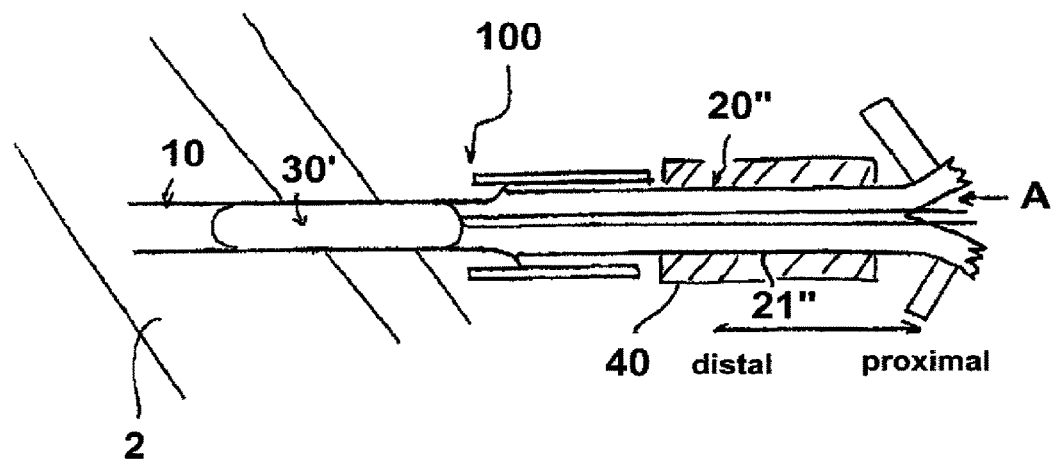
Figure 10:
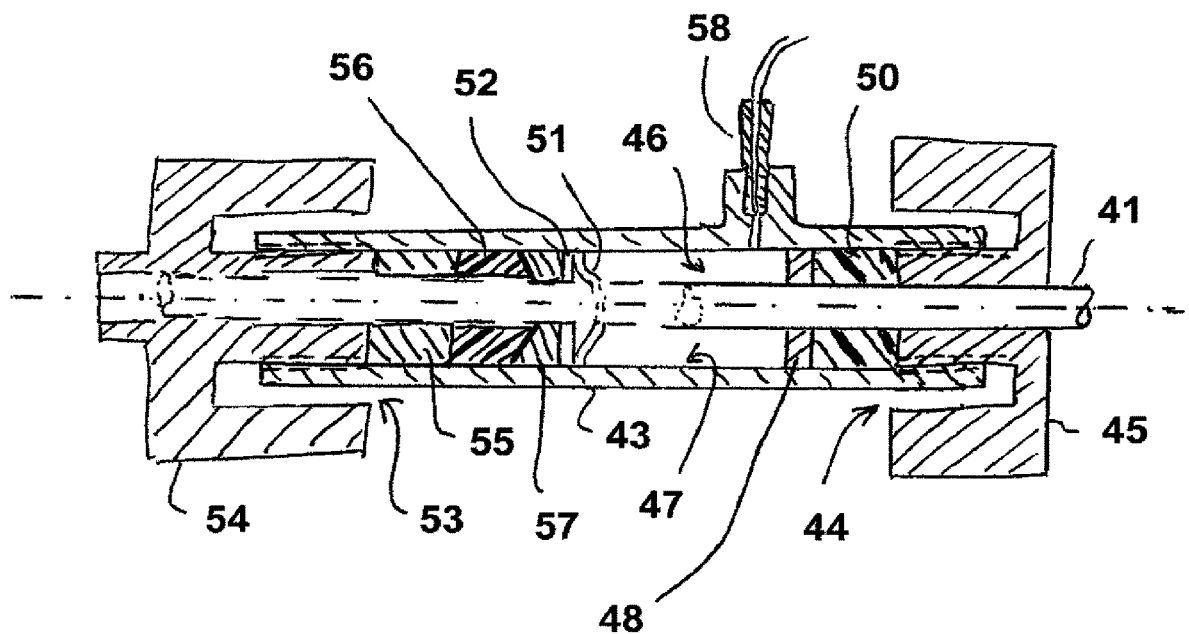
Figure 11:
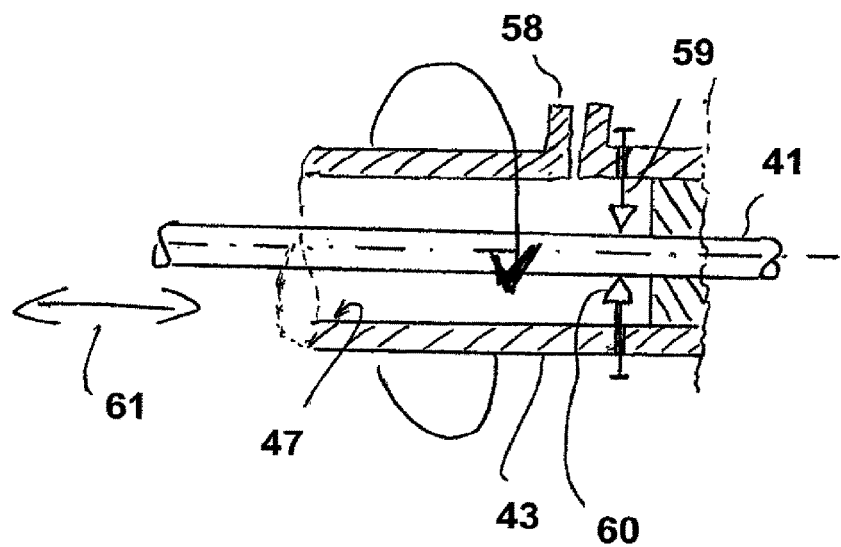
Figure 12:
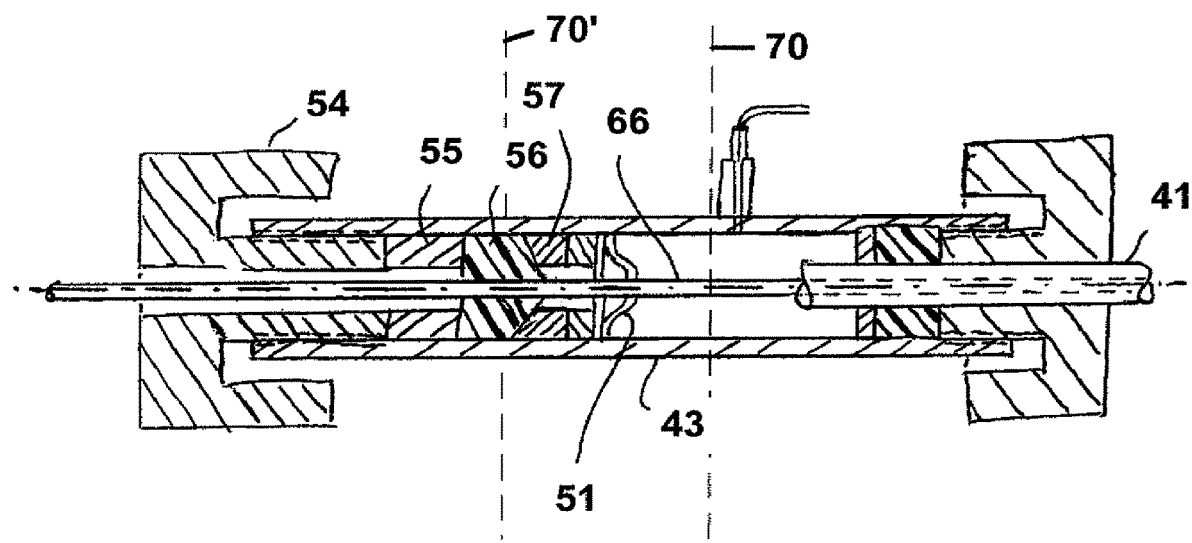
Figure 13A:
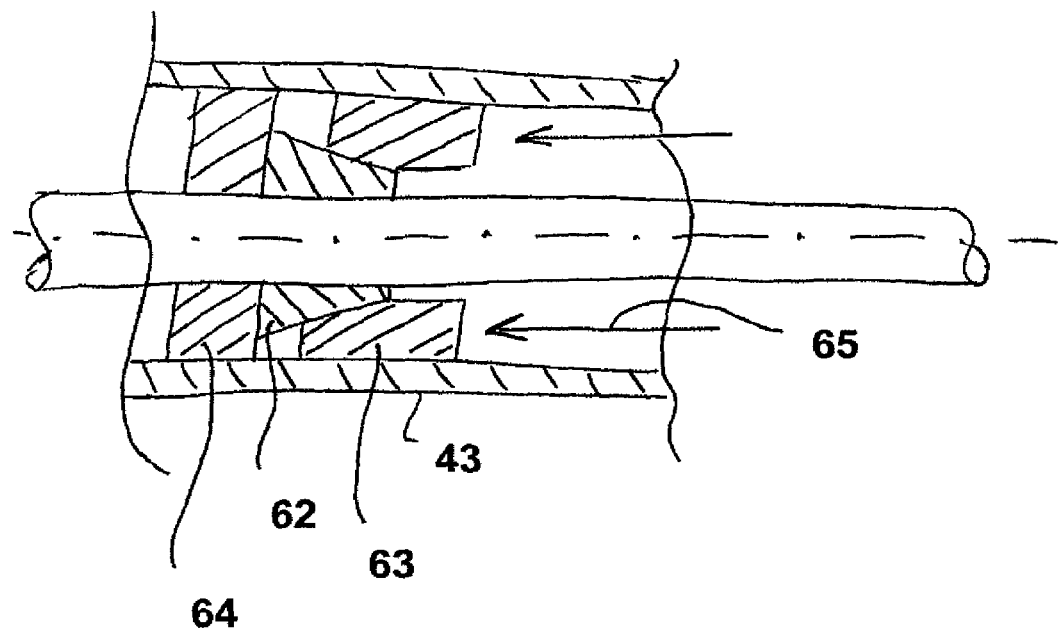
Figure 14:
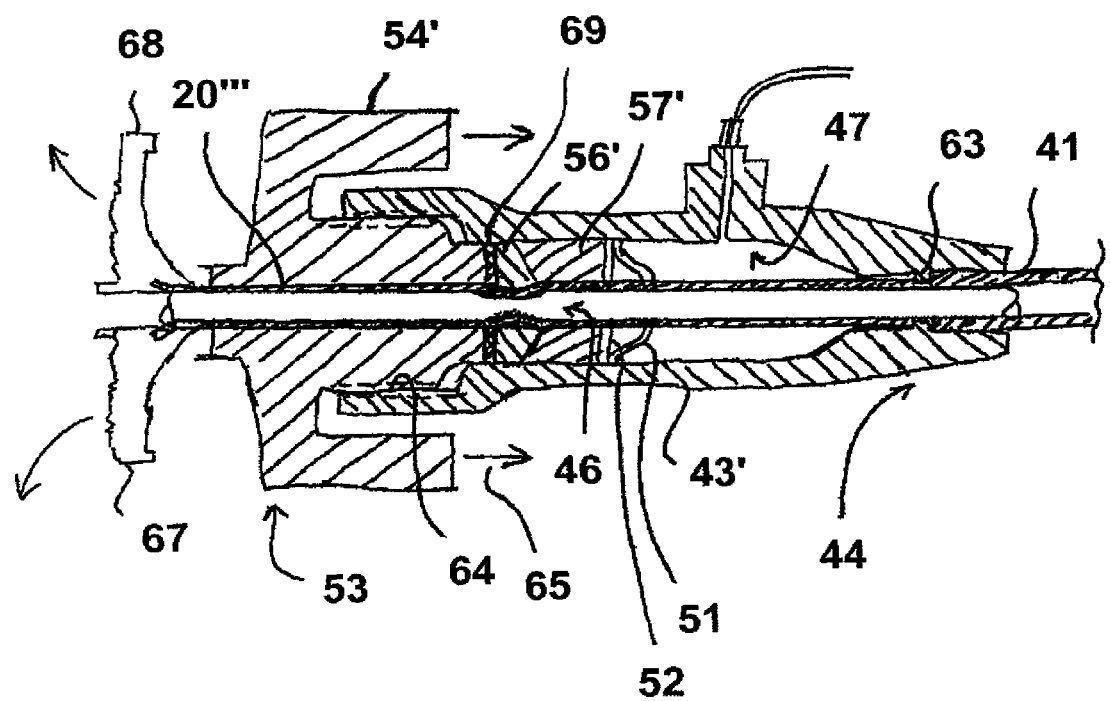
Figure 13B:
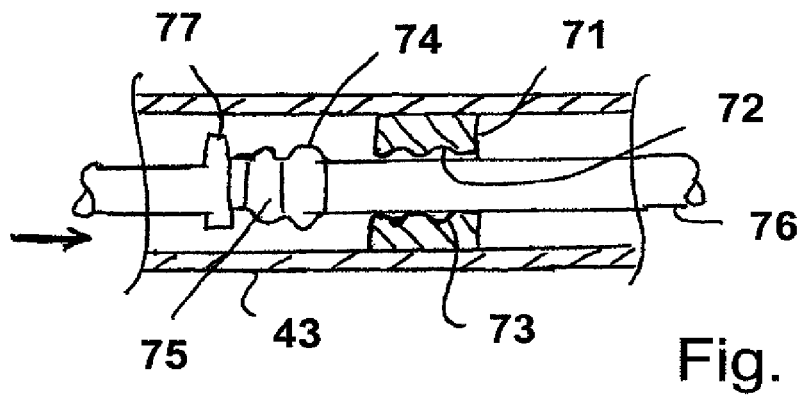
Figure 13C:
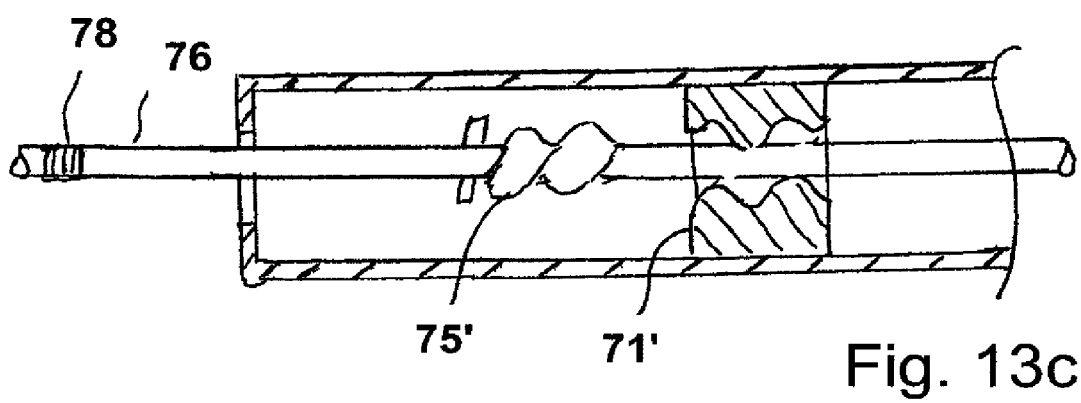
Figure 13D:
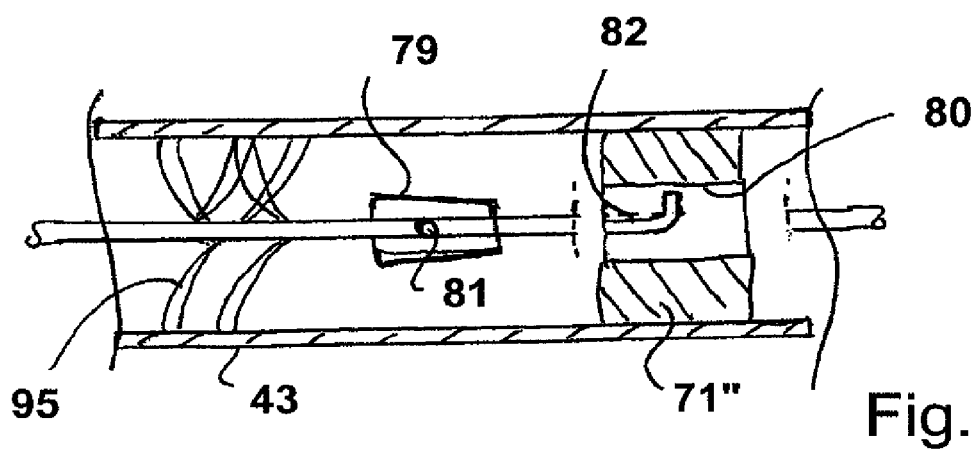
Figure 13E:
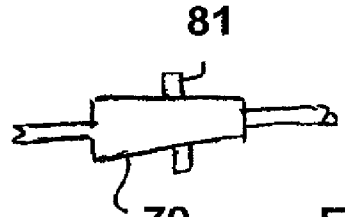
Figure 13F:
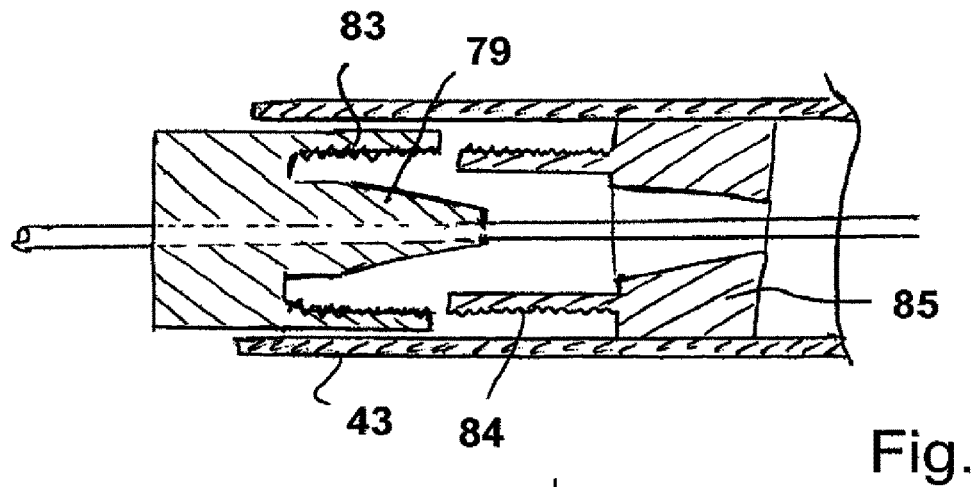
Figure 13G:
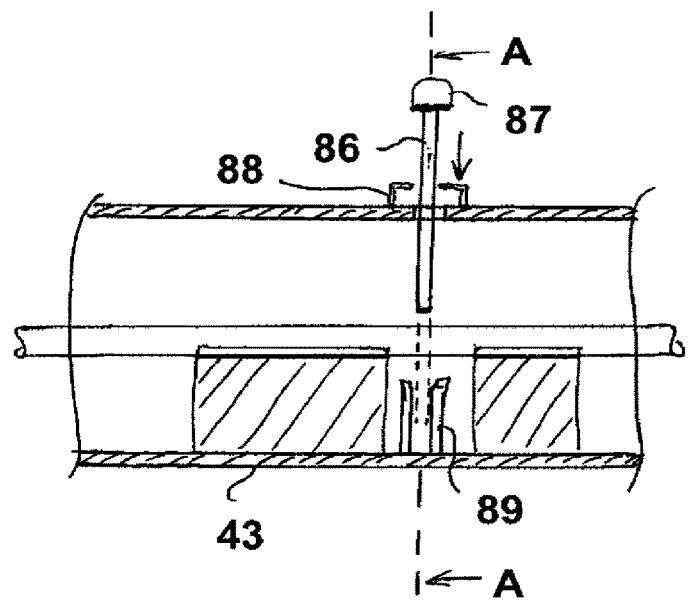
Figure 13H:
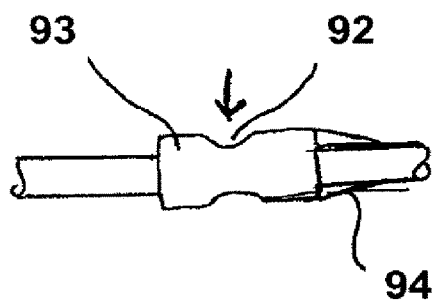
Figure 13I:
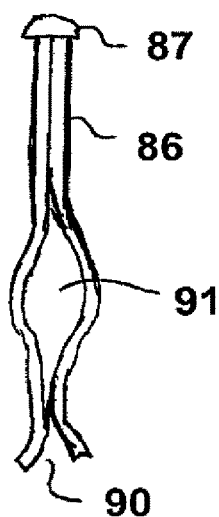
Figure 15:
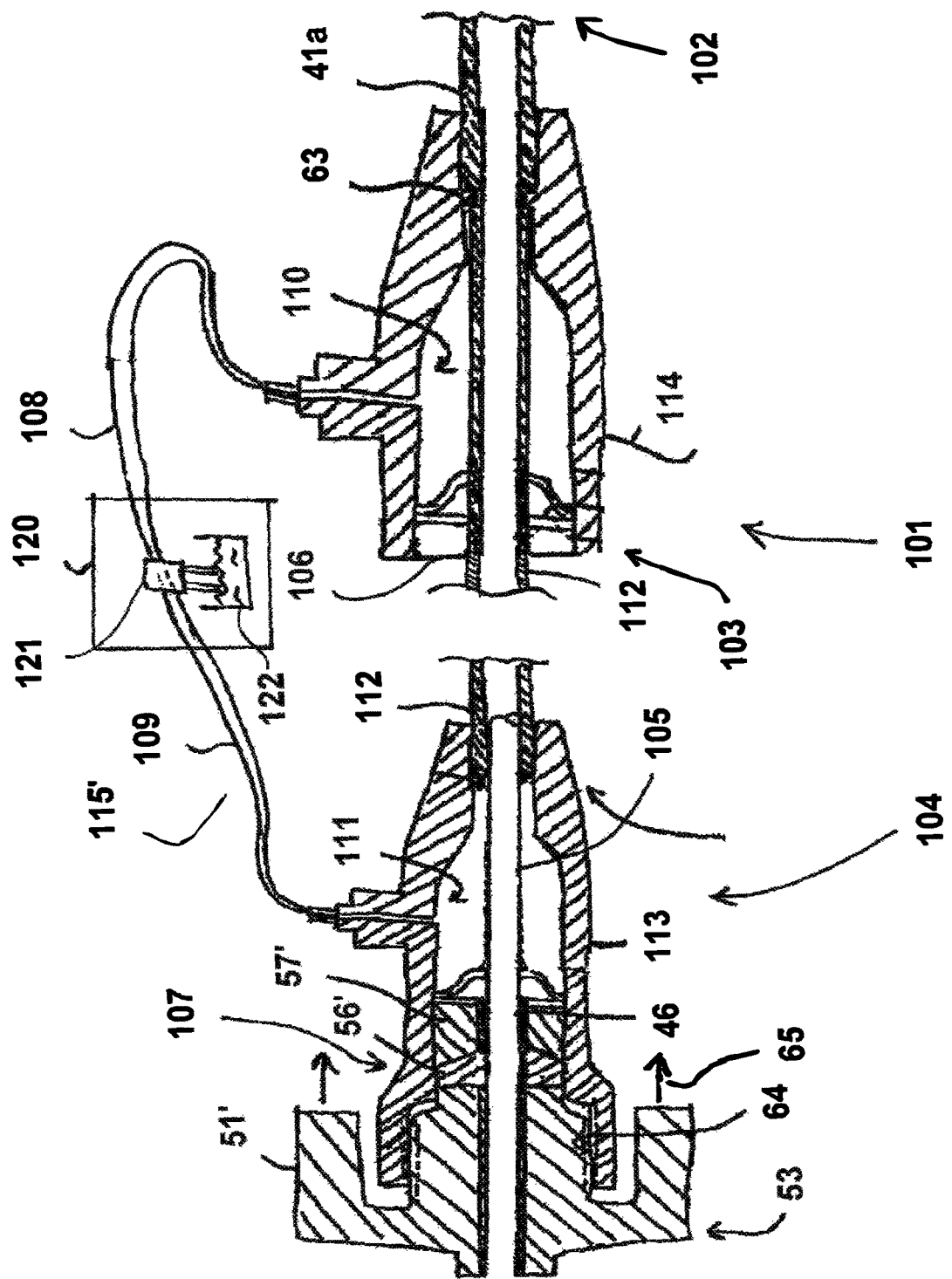
Figure 16:
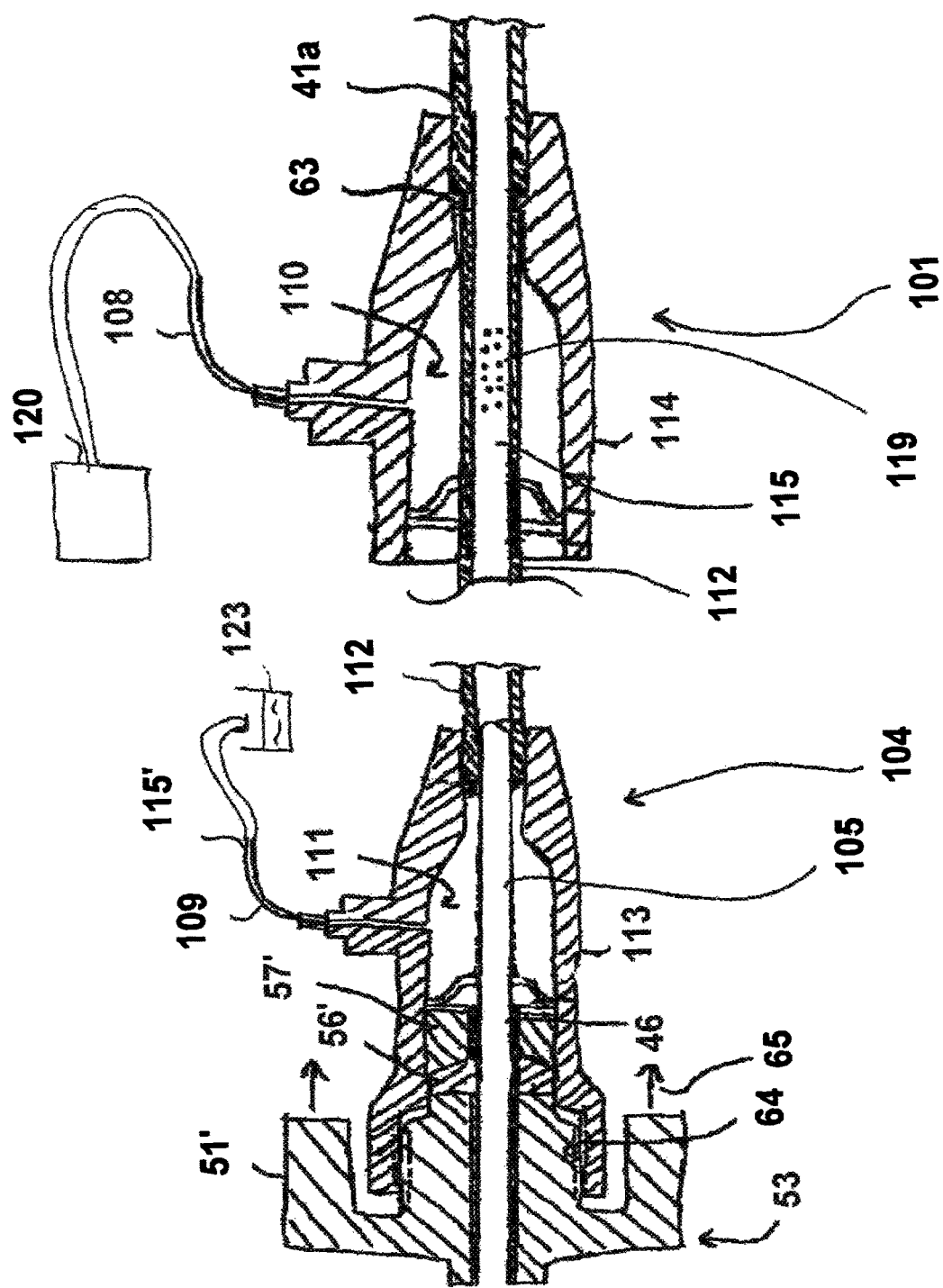
Figure 17:
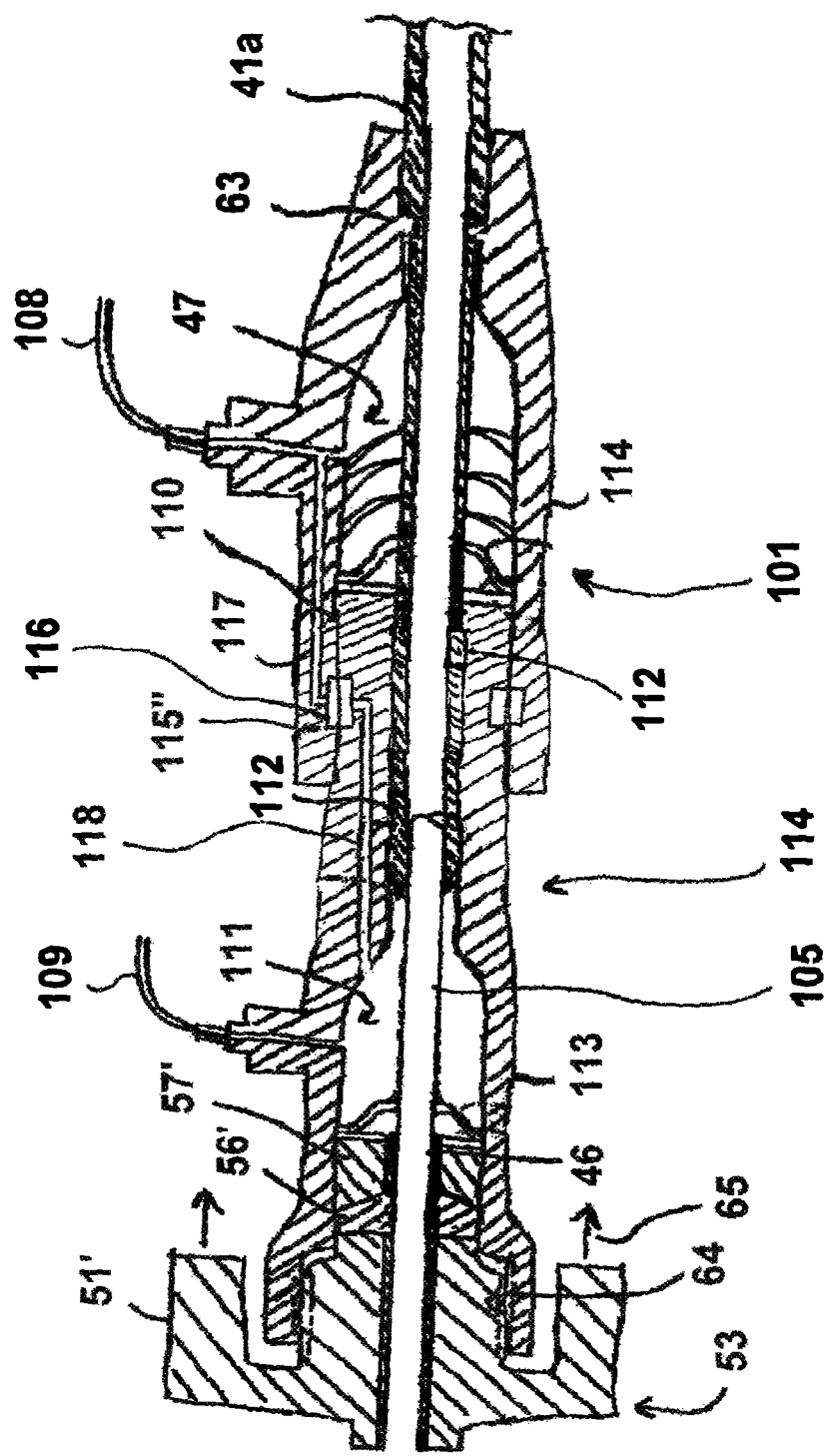
Figure 18:
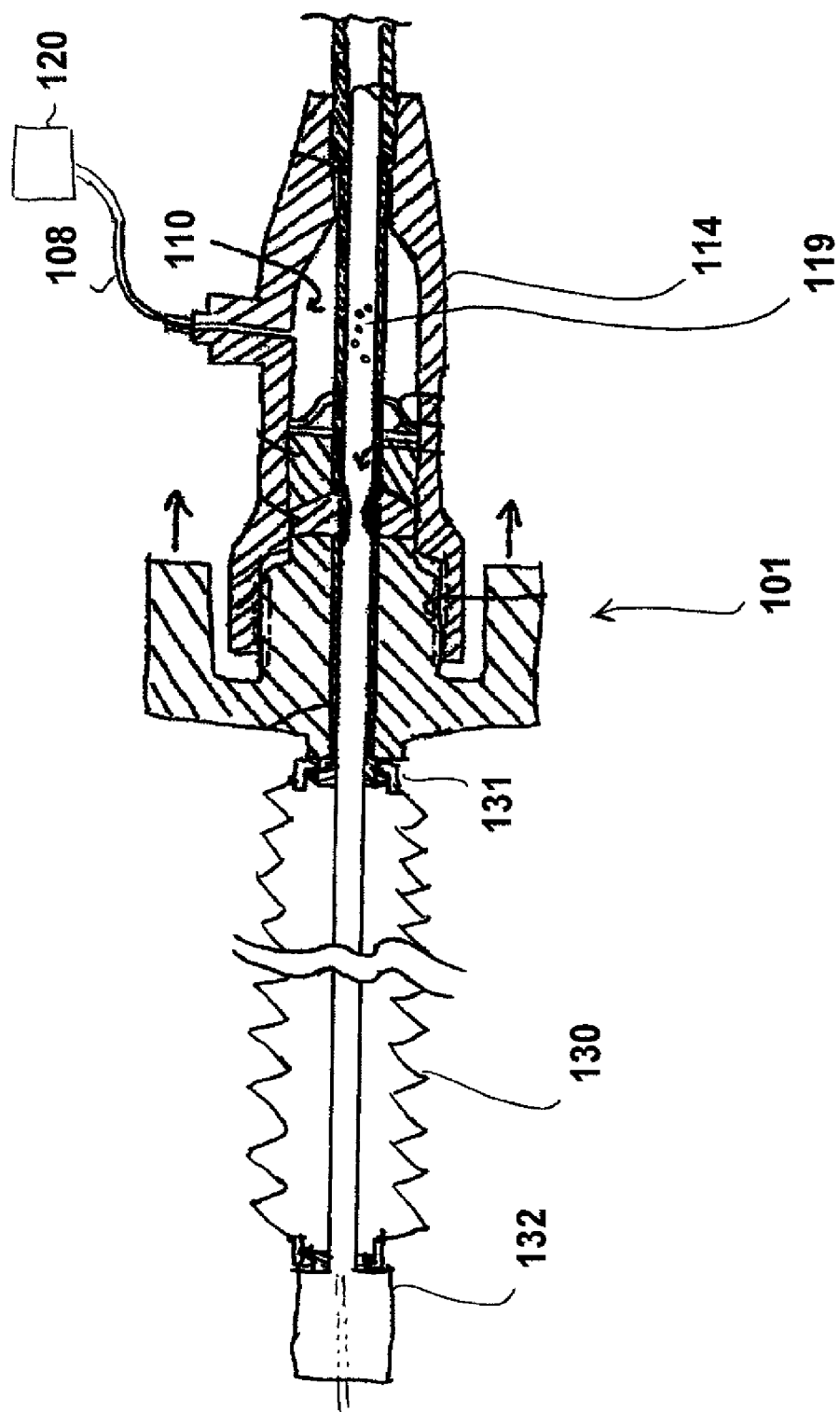

FIG. 1 a schematic overview of a cardiovascular system with an inserted sheath;

FIG. 2 a detailed view of a section of FIG. 1;

FIG. 3 an embodiment of the invention having a first sheath (introducer sheath) and a second sheath (auxiliary sheath);

FIG. 4 an embodiment of a pump;

FIG. 5 a second sheath (auxiliary sheath) with a pump extracted therefrom;

FIGS. 6 and 7 the retraction of a pump into a second sheath (auxiliary sheath);

FIGS. 8 and 9 the transfer of a pump from a second sheath to a first sheath (introducer sheath);

FIG. 10 a longitudinal section of a sheath housing having a tubular section;

FIG. 11 a longitudinal section of part of a sheath housing having a cutting device;

FIG. 12 a longitudinal section of a sheath housing having a clamping device for the tubular section and an additional clamping device;

FIG. 13*a* a longitudinal section of an alternative clamping ring having a conical clamping pad;

FIG. 13*b* a longitudinal section of a clamp connection having flutes and beads, each on the outer surface;

FIG. 13c a longitudinal section having a clamp connection in the form of a threaded connection;

FIG. 13d a longitudinal section having a clamp connection in the form of a conical connection with a bayonet sheath;

FIG. 13e a view of the cone of FIG. 13d rotated 90°;

FIG. 13f a longitudinal section of a luer cone connection having a threaded connection;

FIG. 13g a longitudinal section of a clamp connection having a spring clip that can be guided in the sheath housing, displaced transversally and expanded radially;

FIG. 13h a possible embodiment of the element to be clamped in the region of the clamping point;

FIG. 13i a spring clip of FIG. 13g from a side view, rotated 90° in relation to FIG. 13g;

FIG. 14 a longitudinal section of a sheath housing having a clamping device for a proximally inserted cord-shaped element;

FIG. 15 an introducer sheath and an auxiliary sheath coupled thereto, wherein the flushing devices of the two sheaths are coupled;

FIG. 16 an introducer sheath and an auxiliary sheath coupled thereto, wherein a connection to the interior of the auxiliary sheath is located in the interior of the introducer sheath;

FIG. 17 a sheath assembly, in which the sheath housings of auxiliary sheath and introducer sheath are securely connected; and FIG. 18 an introducer sheath with an auxiliary sheath, which can be received in a sterile tube.

FIG. 19a an axial sectional view of an introducer sheath with an auxiliary sheath and a cord-shaped element/catheter inside the auxiliary sheath, wherein the auxiliary sheath extends inside the introducer sheath;

FIG. 19b an axial sectional view of an auxiliary sheath with a cord-shaped element/catheter inside the auxiliary sheath;

FIG. 19c an axial sectional view of an introducer sheath with a cord-shaped element/catheter inside the introducer sheath.

FIG. 1 shows a schematic illustration of a human cardiovascular system 1. In the region of the groin is one of the femoral arteries 2, which is connected via a major artery to the aortic arch 3, and then leads to the cardiac chamber 4. Using the Seldinger technique, for example, first an introducer sheath 10 is inserted into the femoral artery 2. In this process, first the femoral artery or some other blood vessel is punctured using a steel cannula with a cutting tip, for example. A guide wire 12 is then pushed through the steel cannula inserted through the puncture opening, and is inserted retrograde via the aortic arch 3 into the left ventricle 4. Once the puncturing cannula has been removed, the first sheath 10, embodied as the introducer sheath, which comprises a tubular section 11 and optionally a dilator, not shown here, is threaded onto the guide wire and is inserted through the puncture site into the cardiovascular system, wherein the sheath is inserted a short distance into the lumen of the cardiovascular system or also up to the site where an element to be inserted will be deployed. A fluid pump is then inserted through the introducer sheath 10 into the cardiovascular system.

The tubular section 11 of the first sheath 10 is inserted into the artery such that the proximal end of the first sheath 10 lies outside of the femoral artery and protrudes from the body of the patient, and can therefore be used for inserting a blood pump, for example. It is therefore possible to thread the pump onto the guide wire 12 to allow the pump to be guided with the help of the guide wire up to the left ventricle.

It is also possible to guide the tubular part/section 11 of the first sheath/introducer sheath 10, guided by means of the guide wire, up to the left ventricle, and to then remove the guide wire 12 from the first sheath. Any pump unit can then be guided through the first sheath lumen up to the vicinity of or into the left ventricle 4.

Above, the method is described only in reference to the insertion of a pump into the left ventricle to support cardiac function. However, it will be readily clear to a person skilled in the art that the pump or some other functional element can also be positioned and inserted into other locations in the cardiovascular system of the body.

It goes without saying that, rather than a blood pump/cardiac support pump, some other functional element, particularly a compressible and expandable element, can be inserted using a catheter via the sheath.

FIG. 2 shows the region of FIG. 1 in which the first sheath 10 is guided from the exterior through the tissue of the body into the lumen $L_G$ of the femoral artery 2. The first sheath in this case comprises a tubular section 11, which is connected proximally to a sheath housing 13. The tubular section 11 defines a lumen $L_1$, which has an inner diameter $d_{11}$. Said lumen widens in a trumpet shape toward the proximal end of the tubular section 11, in the region 14.

The sheath housing 13 contains a hemostatic valve that is known in the prior art. Said valve prevents fluid that is held inside the lumen $L_G$ from escaping through the lumen $L_1$ to the outside.

In the illustration of FIG. 3, the first sheath 10 of FIG. 2 is coupled to a second sheath 20. Only a tubular section 21 of the second sheath 20 (auxiliary sheath) is shown, which defines a lumen $L_2$ having an inner diameter $d_{21}$. The distal end of the second sheath 20 has an outer diameter that is such that said end can be inserted into the sheath housing 13. However, the inner diameter $d_{21}$ is greater than inner diameter $d_{11}$.

A pump that is located inside the lumen $L_2$ and is not shown here can then be transferred from the second sheath lumen $L_2$ into the first sheath lumen $L_1$ by applying pressure. The pump is then transported through the first sheath lumen $L_1$ up to the site in the cardiovascular system where the pump will be deployed. In this step, the pump can either be guided on a guide wire or inserted without a guide wire through the first sheath lumen. To protect the pump and the vascular walls as well as the shaft catheter, the first sheath can be fed forward distally up to the site of deployment of the pump before the pump is pushed out.

One possible embodiment of a pump 30 will be specified in greater detail in reference to FIG. 4. The pump 30 comprises a distal pump unit 31 and a shaft catheter 32 that is attached to the proximal end of the distal pump unit 31. The shaft catheter 32 has at its proximal end, which is not shown here, a coupling for coupling the shaft catheter 32 to a drive unit. The drive unit can be located outside of the patient's body and rotates a flexible shaft, which extends inside the shaft catheter 32, which in turn drives the distal pump unit 31. However, the present invention is also suitable for inserting pumps that are differently actuated (by means of an electric motor situated on the pump or by means of a pneumatic turbine arranged in the pump).

The distal pump unit comprises a pump housing 33, which is produced from intersecting nitinol braces. Parts of the nitinol housing are provided with a coating 34, which extends distally and proximally to a rotor 35 arranged inside the housing 33. The rotor is connected to the shaft 36 which extends through the shaft catheter 32 and is thereby placed in rotation. The housing and the rotor are compressible, i.e., the pump is a self-decompressing pump. The pump is expanded once the distal pump unit has been pushed out of the distal end of a sheath. To compress the pump in preparation for implantation, the distal pump unit is retracted into the distal end of a sheath lumen of a second sheath (auxiliary sheath). This sheath lumen has an inner diameter which can be greater than the outer diameter of the shaft catheter.

The rotor can be displaceable in the axial direction in relation to the pump housing, particularly by means of axial displacement of the drive shaft. Conversely, the rotor can also be fixed in the axial direction in relation to the pump housing.

The pump optionally has a discharge tube 37, which defines a flow channel, located proximally to the rotor 35, for the pumped fluid. Located at the proximal end of the discharge tube 37 are outlet openings, which are not described in greater detail.

Of course, the pump can also be switched from pumping operation to suction operation, so that the pump no longer conducts fluid from the distal end to the proximal end, but vice versa.

A more detailed description of a further suitable pump may be found, for example, in document EP 2 047 872 A1.

The functioning of the system will now be specified in greater detail in reference to FIGS. 5 to 9.

FIG. 5 shows a pump 30', which corresponds substantially to the pump 30 according to FIG. 4. For purposes of simplification, details of the pump are not shown. Only the bulbous housing and the "pigtail" which is located distally to the bulbous housing and which prevents the cardiac pump from becoming suctioned to the heart wall are shown. The shaft catheter 32' extends proximally to the distal pump unit 31'. A second sheath 20' is arranged encompassing a region 38' of the shaft catheter 32', said sheath comprising a lumen $L_2$, the inner diameter $d_{21}$ of which is smaller than the diameter of the distal pump unit 31' in the expanded state.

The pump 30' shown in FIG. 5 is a compressible pump, in other words, the distal pump unit 31', which comprises, i.e., the pump housing and the rotor disposed therein, is embodied such that it can be compressed, i.e., its diameter can be decreased. Once a quality assurance inspector or, for example, a doctor has verified the proper functioning of the pump 30', e.g., by observing the rotational movement of the rotor unit located in the distal pump unit 31' during a test run, the distal pump unit 31' is retracted into the lumen $L_2$ of the second sheath 20' by pulling the shaft catheter 32' in the proximal direction. By retracting the pump into the second sheath 20', any bending and/or damage to the shaft catheter and/or the shaft that is located therein is avoided. The pump 30' and the second sheath 20' that encompasses the region 38' of the shaft catheter 32', shown in FIG. 5, form a system 200, which makes it possible to test the functioning of the pump 30' in good time prior to an operation, and to then compress the pump by pulling the distal pump unit 31' into the distal end of the second sheath 20', thereby avoiding damage to the shaft.

Although the system can be implemented both with actively decompressible pumps and with self-decompressible pumps, it is particularly well suited for self-decompressible pumps, i.e., pumps, the distal pump unit of which automatically returns to its original size outside of the sheath.

FIG. 6 shows an intermediate step during retraction of the distal pump unit 30' into the lumen of the second sheath 20'. It is clear that the distal pump unit 30' is compressible and can be brought to a smaller diameter, so that the distal pump unit 30' can be accommodated within the lumen of the second sheath 20'.

Also shown in FIG. 6 is a coupling 39' attached to the shaft catheter 32', which coupling allows the shaft which extends within the shaft catheter to be coupled to the drive unit. Since the outer diameter of the coupling 39' is frequently greater than the inner diameter of the lumen $L_2$, in most cases the second sheath 20' is pushed on in the distal direction from the proximal end of the shaft catheter 32' prior to the mounting of the coupling 39', so that the pump is delivered in the system 200, i.e., the pump is delivered with the second sheath 20', which is located proximally to the distal pump unit 31', and the pre-mounted coupling 39'. FIG. 6 also shows a slight widening of the distal end of the second sheath 20'. The trumpet-shaped expansion 24' facilitates the insertion of the distal pump unit 31' into the lumen $L_2$ of the second sheath 20'.

Finally, in FIG. 7, the distal pump unit 31' as a whole is located inside the lumen $L_2$ of the second sheath 20". The second sheath 20" has two pre-mounted grip units 22", which enable a better hold on and/or removal of the second sheath 20" as the distal pump unit 31' is being retracted into the lumen $L_2$, and/or a better subsequent tearing away. According to the invention, however, an auxiliary sheath which remains permanently connected to the introducer sheath or is held therein can also advantageously be used. Advantageously, if a "pigtail" is provided, this is likewise retracted into the lumen $L_2$, so that the distal pump unit 31' is located inside the lumen $L_2$, along with components of the pump that are disposed distally in relation to the distal pump unit 31'.

FIG. 8 illustrates how the system 200 of pump 30' and second sheath 20" is combined in active connection with the first sheath 10 to form a system 100. First, the second sheath 20" (auxiliary sheath) is inserted with its distal end into the sheath housing of the first sheath 10 (introducer sheath). As soon as the distal tip of the second sheath 20" reaches the opening of the tubular section of the first sheath 10, the pump is transferred from the second sheath 20' into the first sheath 10' by pushing the pump in the distal direction, wherein pushing is accomplished by applying pressure to the shaft catheter 32'. In this process, the diameter of the distal pump unit 31' is further reduced to the inner diameter $d_{11}$ of the lumen $L_1$.

FIG. 9 shows the subsequent step, in which the distal pump unit 31' as a whole is located inside the lumen $L_1$ of the first sheath 10. The fact that the distal pump unit 31' as a whole is located inside the lumen $L_1$ of the first sheath 10 can be indicated by means of a colored marking 50, for example, which is applied to the outside of the shaft catheter 32'.

Assuming the second sheath 20" is embodied as a "peel-away" sheath, it can then optionally be removed from the shaft catheter 32' by tearing away the peel-away sheath from the proximal end to the distal end, and pulling it off of the shaft catheter 32'. The directed tearing away from the proximal end to the distal end can be supported by notches A, but is primarily based on the orientation of the molecular chains of the plastic that is used from the proximal to the distal direction.

Once the sheath has been removed, if applicable, the pump 30' is further guided inside the lumen $L_1$ of the first sheath 10 up to the desired location.

Optionally, the first sheath can also be pushed forward with the distal sheath opening in the immediate vicinity of the deployment site before or after the pump has been inserted. The length of the first sheath is sufficient for this purpose.

A reinforcement of the second sheath 20" is not necessary, particularly when the distal pump unit 31' is retracted into the distal end of the second sheath lumen $L_2$, since the risk that the shaft may break during a pulling movement is substantially reduced.

As the pump is being transferred from the second sheath to the first sheath, as shown in FIGS. 7 to 9, the second sheath can comprise a reinforcing structure in the form of an inserted wire, or the tubular section 21" of the sheath 20" can be made not of a flexible plastic but of a rigid plastic or metal.

A further option for stabilizing the pump and the second sheath involves holding the second sheath 20" by means of a supporting device 40 in the form of a stable outer sleeve and/or in a receiving channel of the introducer sheath as the pump 30' is being pushed forward in a distal direction, i.e., particularly as the pump 30' is being transferred from the second sheath to the first sheath.

In what follows, another possible variant of a method for inserting a pump into a left ventricle of the heart will be described. As a preparatory measure, the pump is first filled with sterile physiological saline solution and is thereby completely vented of air. The auxiliary sheath, which is disposed proximally to the distal pump unit, is then pushed forward up to a discharge tube, if one is provided. The auxiliary sheath has a diameter of 10 Fr, for example. Once the auxiliary sheath has been advanced up to the discharge tube, the auxiliary sheath is encompassed by a sleeve-like, supporting device. The distal pump unit is then retracted, optionally with a slight rotational movement, into the auxiliary sheath by exerting a pulling movement in the proximal direction on the shaft catheter. The pump is pushed far enough into the auxiliary sheath that any pigtail that exists is likewise concealed inside the auxiliary sheath. These steps allow the proper functioning of the pump to be tested prior to a surgical operation, and allow the pump to be inserted into a sheath only after said testing, without requiring such action to be performed under pressure of time. The vascular system is punctured for insertion of the first sheath only after said testing, for example. To save time, however, this also allows an assistant to prepare the pump while the surgeon performs puncturing in parallel.

Once a 9 Fr introducer sheath has been inserted up to the left ventricle of the heart, for example, a dilator, if one is provided, may optionally be pulled out of the introducer sheath and removed therefrom.

The pump, which is held inside the auxiliary sheath and which is initially encompassed by the sleeve, for example, is then pushed into the sheath housing of the introducer sheath until the tip of the auxiliary sheath strikes a mechanical stop. The pump is then transferred from the auxiliary sheath into the tubular section of the introducer sheath by applying pressure to the shaft catheter. Once the distal pump unit as a whole has been transferred into the introducer sheath, as can be ascertained on the basis of an optical marking on the shaft catheter shaft, for example, the auxiliary sheath can be left inside the introducer sheath, or optionally, a peel-away sheath can be torn away and removed from the shaft catheter. The pump is then pushed forward inside the first sheath (introducer sheath) up to the left ventricle. The first sheath is then pulled back out of the left ventricle up to the start of the descending aorta.

The positioning of the distal pump unit in the left ventricle can be verified, for example, by x-ray imaging. For this purpose, a marking detectable by x-ray is located on the pump housing or in the vicinity thereof, for example, on the catheter, or the pump housing itself is detectable by x-ray. The outlet region of the pump, i.e., the outflow openings in a delivery tube, should likewise lie in the region of the ascending aorta. This can also be verified by means of a marking that is detectable by x-ray. If a pigtail catheter tip is present, it should touch the tip of the left ventricle.

To remove the pump from the ventricle, the pump is drawn back into the introducer sheath by applying tractive force to the shaft catheter, and is removed, compressed, from the arterial vascular system. If the first sheath has already been shortened, the pump can also first be drawn back a short distance into the shaft catheter in order to compress the pump. For this purpose, the shaft catheter can have a retraction funnel, into which the pump can be retracted by pulling on the drive shaft. The first sheath and other remaining components are then removed from the cardiovascular system.

With the invention, it is particularly advantageous to use a long sheath particularly as the introducer sheath in the implantation and explanation of the pump. The long sheath serves not only for inserting the pump into a lumen inside the body, as is customary in the prior art, but also for guiding the pump through the lumen of the sheath into the area of the deployment site. In this connection, it is advantageous in the medical field for the sheath to have a length of between 40 and 120 cm. The length is determined by the subsequent deployment site of the pump and the physique of the patient.

Once the pump, together with the long sheath, is removed from the lumen of the body, bleeding from the femoral artery is stopped using a compression bandage. Alternatively, the pump can be removed from the lumen of the long sheath. An additional guide wire can then be positioned through the lumen of the sheath, via which wire a device for closing the puncture can be guided once the sheath has been removed. This results in improved hemostasis.

FIGS. 10 to 13 specifically show a variant of the first sheath according to the invention having one or more clamping devices for securing a tubular section 41 in a sheath housing 43.

FIG. 10 also shows a longitudinal section of a sheath housing 43 having substantially the form of a cylindrical sleeve which is closed at least at the distal end 44, which faces away from the body of the patient, by means of a pressure screw 45. The sheath housing 43 has a continuous receiving channel 46 for a tubular section 41 of the sheath. In the diagram of FIG. 10, the tubular section 41 is indicated by a solid line up to the flushing chamber 47 of the receiving channel 46, and is indicated by a dashed line proximally thereto. This indicates that the tubular section 41 can be axially displaced in relation to the sheath housing 43 within the receiving channel 46, or, in other words, that the sheath housing 43 is displaceable on the tubular section 41.

The sheath shown here can be used, for example, as an introducer sheath (first sheath).

To insert a functional element, for example, a pump, into the first sheath, the tubular section 41 is generally pulled in the distal direction far enough out of the sheath housing 43 or is positioned during the production of the first sheath such that it terminates approximately at the height of the first stop piece 48, and is then clamped in place, for example, by actuating the pressure screw 45. A second sheath with a retracted pump, as described above, can then be pushed forward up to this point, in order to then move the pump through from the second sheath into the first sheath.

The first clamping device comprises the first pressure screw 45, a first clamping ring 50 made of an elastomeric material, and the first stop piece 48 as fastening means. A sliding layer or a rotating seal ring 69 can be provided between the clamping ring 50 and the pressure screw 45.

The pressure screw is screw-connected by means of external threading to the distal end 44 of the sheath housing 43, in the region of the overlap therewith. Manual rotation of the pressure screw 45 therefore causes the pressure screw to move in the axial direction, resulting in an axial compression or expansion of the clamping ring 50. In the case of axial compression, the clamping ring 50 tends to maintain its volume radially toward the inside and to expand toward the outside, thereby clamping the tubular section 41, since at its proximal side, the ring meets resistance against the first stop piece 48.

The tubular section 41 is thereby fixed axially in relation to the sheath housing 43. This fixation can be released simply by releasing the pressure screw 45, so that the tubular section 41 can then be displaced a short distance axially inside the sheath housing 43. To this end, in its relaxed state the clamping ring can have an inner diameter which is equal to or greater than the diameter of the first sheath.

Thus, if the tubular section 41 is first advanced as far as possible into the body of the patient in order to allow the pump to be inserted, protected by the sheath, up to the deployment site, for example, to a ventricle of the heart, then once the pump has been delivered, the tubular section 41 is withdrawn, and the sheath as a whole projects a relatively great distance out of the body of the patient. The clamping device 48, 45, 50 can then be released and the sheath housing 43 can be advanced closer to the body of the patient on the tubular section 41. In this step, the tubular section 41 then extends all the way through the sheath housing 43 and optionally protrudes out of said housing in a proximal direction. Using means which will be described in greater detail further below, the tubular section 41 can then be partially detached in order to remove the excess length.

To produce a better seal, a so-called combined hemostatic valve, consisting of a dome valve 51 and a valve plate 52, is provided inside the sheath housing 43. The valve plate closes off the sheath housing 43 when neither the tubular section 41 nor a shaft catheter extends through the receiving channel 46 at this location, whereas the dome valve 51 is optimized to produce a tightly fitting seal around a cord-shaped element, for example, the tubular section or a catheter.

At the proximal end 53 of the sheath housing 43, an additional pressure screw 54 is provided, which in principle functions in the same manner as the first pressure screw 45 and which effects, via a clamping pad 55, the compression of a second clamping ring 56 in relation to a second mechanical stop 57. A catheter or an inserted auxiliary sheath can thereby be clamped into the introducer sheath. As a special feature it should be mentioned here that the second clamping ring 56 extends in the form of a cone at its distal end, which favors a deformation radially toward the inside when axial pressure is exerted by means of the pressure screw 54. The second stop 57 is designed accordingly in an opposing conical shape. However, a clamping ring 56 that is non-conical and instead has a rectangular or round cross-section can likewise be used at this location.

In FIG. 10, a flushing device 58 is indicated schematically, which allows the flushing chamber 47, which is the interior of the sheath housing, to be flushed with a fluid that prevents bacteria from entering the patient's body through the first sheath. This flushing is particularly effective if the tubular section 41 terminates in the flushing chamber 47 or at the distal end thereof, so that the flushing fluid reaches both the exterior and the interior of the tubular section 41.

FIG. 11 illustrates by way of example the configuration and mode of functioning of a cutting device according to the invention.

If no predetermined breaking points are provided, pre-cut or provided in some other way, for example, by a predetermined molecular structure or localized weakening of the wall thickness of the tubular section 21, these can be introduced appropriately by means of a cutting device during use of the first sheath. In FIG. 11, a cutting device with blades 59, 60 is provided in the region of the flushing chamber 47 of the sheath housing 43, which blades cut said housing in the circumferential direction when the sheath housing is rotated in relation to the tubular section, for example. Cuts may also be made in the axial direction.

For this purpose, the blades 59, 60 can also be arranged such that, when the tubular section 41 is moved in an axial direction, as indicated by the arrow 61, they cut in the longitudinal direction. It is also possible to provide blades for cutting in the circumferential direction and one blade for cutting in the longitudinal direction.

FIG. 11 further indicates that the blades 59, 60 can be moved in the direction radially toward the tubular section 41 by actuating said blades from the exterior of the sheath housing 43. At said location, a guide extending in the radial direction for one or more blade holders, a corresponding seal, and a spring mounting can be provided, so that bacteria are prevented from penetrating through this displacement device for the blades, and in the non-actuated state, the blades are located at a distance radially from the tubular section 41. Once the first sheath has been used, pressure can be exerted manually on the blades, and the part of the tubular section 41 that is no longer needed can be cut off. A stop, not shown here, prevents the cutting depth from exceeding a critical level and thereby damaging a catheter that may be located inside the sheath.

The blades shown can also form a cutting device for a second sheath.

FIG. 12 illustrates an advantageous use of the second clamping device at the proximal end of the sheath housing 43 once the tubular section 41 has been shortened, and when a shaft catheter 61 leads out of the proximal end of the tubular section 41 and out of the sheath housing 43, up to a coupling device, not shown, for a driveable shaft of a pump. The shaft catheter is sealed in the above-mentioned dome seal 51, and the clamping device comprising the elements of the second pressure screw 54, and the second clamping ring 56, which is compressed axially in relation to a second stop 57 by means of the clamping pad 55, expands radially inward far enough that it clamps the shaft catheter 61, which has a substantially smaller outer diameter than the tubular section 41 or a second sheath, particularly also sealing said catheter. However, said clamping does not prevent the rotation of the shaft that is rotatable therein. In this manner, both the tubular section 41 and the shaft catheter 61 that projects therefrom can be fixed inside the sheath housing 43.

The second clamping device is likewise suitable for fixing the second sheath with the second clamping ring 56 during the insertion of a second sheath into the sheath housing 43 such that said second sheath is adequately fixed in relation to the sheath housing 43 and especially also in relation to the tubular section 41 to allow the shaft catheter 61 to be pushed through.

The first and second clamping rings 50, 56 can be made of an elastomer, for example, a rubber or silicone elastomer, and can therefore be fully flexible, but deformable with an incompressible volume. However, a flexible foam which is partially compressible in terms of volume may also be used at this location. In place of a clamping ring 56, a radially displaceable spring clip can also be provided for producing a clamping connection, as is illustrated in FIGS. 13g, 13h and 13i and will be specified in greater detail further below. A corresponding spring clip can be provided in addition to or in place of a clamping ring. The spring clip can be provided in the region of the dashed lines 70 in FIG. 12. However, the spring clip may also advantageously be provided in the region of the dashed line 70', since this region lies proximally to the seal 51, and therefore, it is not necessary to exert particularly high stresses on the seal of the sliding arrangement of the spring clip.

FIGS. 13a to 13i show clamping devices and/or securing devices for sheaths, which can be used alone or in combination in an introducer sheath and/or an auxiliary sheath.

FIG. 13a shows a schematic illustration of a type of clamping ring 62, which can be made, for example, of a plastic or a metal, and is particularly slotted and can therefore be radially compressed. The slotted clamping ring 62 has a conical external contour, against which the conical contour of a clamping pad 63 presses in order to compress the clamping ring radially as soon as an axial compressive force is exerted on the clamping pad 63 in the direction of the arrow 65, for example, by means of a pressure screw as described above. The slotted clamping ring 62 is secured axially by means of the stop piece 64.

FIG. 13b shows an adapter piece 71 inside a sheath housing 43, which has a through channel 72, wherein continuous flutes and beads 73 are provided on the cylindrical outer surface of the through channel 72, which match flutes and beads 74 on a mating adapter piece 75 on the element 76 to be clamped. The mating adapter piece 75 can be inserted into the adapter piece 71 and snapped in flexibly, where it is held in place, advantageously forming a seal. A stop piece 77 prevents the element 76 from being inserted too far, and allows the snap connection to be sensed haptically.

FIG. 13c shows a configuration similar to that of FIG. 13b, wherein the adapter piece 71' and the mating adapter piece 75' are each equipped with a thread, rather than concentric, continuous flutes and beads. The mating adapter piece 75' can be moved into the adapter piece 71' by rotating it, however it is also conceivable to overcome the threading and insert said adapter axially. A visible marking 78 is provided on the element 76 to be clamped, to allow the target position to be identified. However, a shape marking may also be provided, which allows the target position to be sensed haptically or acoustically, or a mechanism may be provided for actuating an electrical contact to emit a signal when the target position is reached/left.

FIG. 13d shows a cone 79 on the element 76 to be clamped, which cone fits into a conical recess 80 in the adapter piece 71' forming a seal. The cone 79 has one or more peripheral pins 81, which are guided in gates 82 on the inner circumferential surface of the recess 80, and serve to form a bayonet-type sheath. Conversely, a pin may also be provided on the outer cone and a gate on the inner cone. A so-called luer sheath may be formed while maintaining the corresponding standard in the connection of sealing cone with sheath. Rather than the bayonet sheath, a threaded connection may also be provided in conjunction with the cone system.

FIG. 13e shows a rotated side view of the cone 79 with two pins 81.

FIG. 13f shows a cone system having a cone 79' and a threaded nut 83 that encompasses said cone. The threaded nut 83 can be screwed onto a thread of the pipe socket 84, which is connected to the adapter piece 85. The adapter piece 85 is securely incorporated into the sheath housing 43 of an introducer sheath, and has an inner cone. The threaded nut 83 can also be embodied as a cap nut which is freely rotatable in relation to the cone 79'.

FIG. 13g shows a sheath housing having a radially displaceable spring clip, which can be actuated by means of a push button 87. A stop 88 is provided, which stops the push button 87 in the target position. In addition, an optically detectable marking may also be provided on the spring clip. As the spring clip 86 is being moved into the sheath housing, it enters an opposite guide 89. Prior to this, the spring clip is elastically expanded when it strikes the element 76 to be clamped. Said spring clip has an intake opening 90 for this purpose, as shown in FIG. 13i. As insertion continues, the holding region 91 comes to rest around the element to be clamped. As is clear from FIG. 13h, said element can have a continuous groove or flute 92, or a collar 93, which has such a flute 92. In this variant, the functions of clamping and sealing the element to be clamped are separate.

Conversely to the described functioning method, clamping may also be produced by advancing the spring clip all the way into the sheath housing 43 and only then axially inserting the element to be clamped, for example, a catheter or a second sheath. In this case, the conical guide bevel 94 allows the collar 93 to be inserted along with the element to be clamped into the spring clip 86, and held in place there.

In principle, the element to be clamped/a second sheath can also be held in a first sheath by flexible, self-sheathing vanes, fins, or teeth, which, when the element is pulled out of the sheath, sheath said element or make pulling it out significantly more difficult. Such vanes are illustrated schematically on the left side of FIG. 13d and are identified by reference sign 95.

FIG. 14 shows a sheath housing 43' of an introducer sheath, which has in its interior a receiving channel 46 for a sheath and/or a catheter. At its distal end 44, the sheath housing 43' has a tubular section 41 that is fastened to said end, which can be glued, cast, or otherwise fastened, for example, in an opening of the sheath housing. The tubular section 41 is inserted into the opening of the sheath housing 43' up to a mechanical stop 63.

A second sheath 20''' (auxiliary sheath) is inserted from the proximal end 53 of the sheath housing 43' into the receiving channel 46 far enough that it terminates distally at the mechanical stop 63. In one embodiment, the system can also be designed such that the second sheath 20''' terminates directly at the tubular section 41. A functional element in the form of a pump with a hollow catheter, for example, is retracted into the second sheath 20''', no more of which is illustrated.

To transfer the catheter with the pump from the second sheath 20''' into the tubular section 41 of the first sheath 43', 41, the two sheaths are aligned coaxially to one another within the receiving channel 46, and the second sheath 20''' is fixed in place by means of a clamping device. The clamping device has a flexible clamping ring 56', which is embodied as conical in shape at its distal end and is forced against a mechanical stop 57'. For this purpose, axial pressure is exerted on the clamping ring 56' by means of a pressure screw 54' having external threading 64. For this purpose, the pressure screw 54' is screwed into the opening in the tubular part of the sheath housing 43', so that it moves axially in the direction of the arrow 65.

To reduce the friction between the rotating pressure screw 54' and the clamping ring 56', a rotating seal ring 69, for example made of PTFE or some other plastic having good sliding properties, can advantageously be provided.

The clamping ring 56' is made, for example, of an elastomer, and expands in a radial direction under axial pressure thereby clamping a cord-shaped element, which is located in the receiving channel 46. In the clamping region, the element to be clamped can have one or more continuous beads, lands, grooves or flutes or edges, for example, in order to improve the clamping effect. A collar may also be provided on the element for this purpose. The second sheath 20''' has a wall thickness of between 0.3 and 0.7 mm, and is made of a material that is sufficiently stable that under radial pressure, the second sheath can be clamped without the catheter extending therein also being clamped at the same time. This allows the catheter to be easily pushed out of the proximal end of the second sheath 20''' into the tubular section 41. The second sheath 20''' is sealed by a combined plate and dome seal 51, 52 in a flushing chamber 47.

Once the functional element, for example, the pump, has been transferred with the catheter from the second sheath 20''' into the tubular section 41, the second sheath can be torn away using the manual tabs 67, 68 and removed. For this purpose, the second sheath can have a weakened area or a notch along its axial direction or a correspondingly pre-defined molecular structure, which allows it to be torn away longitudinally up to the distal end of the second sheath, and allows the second sheath to be removed accordingly. To tear said sheath away, it may be expedient to release the clamping device 54', 56', 57'.

Once the second sheath has been removed or partially removed, the clamping device 54', 56', 57' can be clamped tightly enough that the catheter having a smaller diameter is clamped in the receiving space 46 as a result of the additional radial compression of the clamping ring 56'. The catheter and therefore also a pump to be implanted is thereby fixed at the distal end of the catheter in the axial direction in relation to the first sheath and therefore in relation to the body of the patient.

However, the second sheath (auxiliary sheath) can also be embodied such that it can remain in the introducer sheath. In that case, adequate sealing and flushing capability should also be ensured, as will be specified in greater detail below.

A perceptible stop is implemented by means of formations in the sheath housing, which are not shown here, for each of the different end positions of the pressure screw which correspond to the different diameters to be clamped, so that the user senses a clearly increased rotational resistance with actuation of the screw when the respective clamping position is reached.

Following an initial phase in which the assembly becomes mechanically settled and warms to the body temperature of the patient, the clamping device can be released and the catheter readjusted and then refastened. Everywhere in the described construction where two cylindrical elements are inserted one into the other forming a seal, a conical seal having a cone angle of a few degrees can be advantageously used, as is known, in principle, in the medical field.

The described embodiment of a sheath allows an implantable heart pump, for example, to be transferred from a second sheath, in which it can be kept ready following an initial inspection, into a first sheath, which leads into the body of a patient, without problems and with low complexity and high reliability.

FIG. 15 shows an introducer sheath 101 on the right side of said figure and an auxiliary sheath 104 on the left side, the tubular part 112 of which can be inserted into the introducer sheath 101 and clamped in place there.

The introducer sheath 101, like the auxiliary sheath 104, corresponds substantially to the sheath illustrated in FIG. 14 and described in this context.

The entire sheath assembly illustrated in FIG. 15 comprises the introducer sheath and the auxiliary sheath and is suitable for inserting a cord-shaped element/catheter 105 through the auxiliary sheath 104 into the introducer sheath 101 and through said introducer sheath into the body of a patient.

The introducer sheath 101 further has at its distal end 102 a tubular part 41a, which is fixed forming a seal in the proximal part 103, which forms a sheath housing 114. The tubular part 112 at the distal end of the auxiliary sheath 104 can be inserted into the introducer sheath 101 and pushed up to a stop 63 in front of the tubular part of the introducer sheath. The stop 63 can simultaneously form an axial stop for the tubular part 112 of the auxiliary sheath and for the proximal end of the tubular part 41a of the introducer sheath, wherein the tubular parts 112, 41a can have the same inner diameter as the flange-type stop 63. The stop 63 is formed in the housing wall of the sheath housing. The introducer sheath has first fastening means 106, which can be similar in design, for example, to the second fastening means 107 of the auxiliary sheath 104 and which has been described in greater detail in reference to FIG. 14 as a clamping device. In principle, however, the first and second fastening means can comprise each of the types of fastening means shown by way of example in FIGS. 13a to 13j.

In order to keep the area of transition between the auxiliary sheath and the tubular part of the introducer sheath within the inner chamber 110 of the housing 114 of the introducer sheath sterile, and to allow said area to be flushed for this purpose, a flushing device 108 is provided with a corresponding flushing tube and an opening provided in the wall of the housing 114. The flushing device is connected to a flushing medium source 120, which comprises a pump 121 and a reservoir 122, for example. The auxiliary sheath 104 likewise has a flushing device 109, which comprises a flushing tube and an opening in the wall of the housing 113. Via this flushing device 109, the housing interior 111 of the auxiliary sheath, and thereby the area of transition from the catheter 105 into the tubular part 112 of the auxiliary sheath, can be flushed and kept sterile.

The first flushing device 108 is connected, for example, to the second flushing device 109 via the flushing medium source 120. It can thereby be provided that the pump 121 conveys flushing medium into both the first flushing device 108 and the second flushing device 109, conveying said medium into the inner chambers of the housings 113, 114.

FIG. 16 shows a variant in which the flushing medium source 120 supplies flushing medium into the interior 110 of the housing 114 of the introducer sheath 101 via the first flushing device 108, wherein the tubular part 112 of the auxiliary sheath fixed inside the introducer sheath has at least one outer-surface opening 119 in the inner chamber 110, for example, an outer-surface perforation consisting of multiple openings, through which the flushing medium can enter into the tubular part 112 and can flow through this axially into the housing interior 111 of the housing 113. Therefore, the flushing medium can actively travel from the flushing medium source 120 through the introducer sheath 101 into the auxiliary sheath 104. In such a case, the structural devices of the second flushing device 109 can serve to vent the auxiliary sheath, for example, or to discharge the flushing fluid there, in order to collect this in a collecting tank 123. In this case, the interior of the tubular part 112 of the auxiliary sheath forms a part of the auxiliary flushing channel 115' for connecting the two sheaths. In the variant shown in FIG. 15, such an auxiliary flushing channel 115 is provided by the infeed tubes of flushing devices 108 and 109 and/or the connection thereof.

The outer-surface openings/recesses 119 in the tubular part 112 of the auxiliary sheath can also be introduced into the part 112 only after the catheter has been inserted into the body of the patient, for example. A cutting assembly, as illustrated in FIG. 11, for example, may be used for this purpose.

Finally, FIG. 17 shows a design in which the sheath housing 114 of the introducer sheath is securely connected to the sheath housing 113 of the auxiliary sheath 104. The two sheath housings are securely inserted one inside the other in a cylindrical or slightly conical subregion. A threaded connection or a bayonet connection may also be provided.

A circumferential groove 116 is provided, which is formed, for example, as in the illustrated version by circumferential grooves in the housing 113 of the auxiliary sheath on one side and in the housing 114 of the introducer sheath on the other side. However, it can also be sufficient to provide a circumferential groove in only one of the housings. The circumferential groove or both circumferential grooves are connected via one channel-like recess 117, 118 each, which extends through the wall of the respective housing 114, 113, to a first flushing device 108 and/or to the interior of the respective sheath housing 114, 113. As a result, in the variant shown, both the interior of the housing 114 and the interior of the housing 113 can be flushed via the first flushing device 108. In this case, the second flushing device 109 is used for venting and for discharging flushing fluid, according to FIG. 16. Conversely, however, flushing of both houses may also be provided by the second flushing device. Due to the circumferential groove 116 that is provided, it is not necessary to adhere to a precise angular position in connecting the two sheath housings; rather, it is necessary only for the axial positions of the two sheath housings 101, 104 to be maintained relative to one another. This can be ensured, for example, by a fixed stop on one of the two sheath housings.

In addition, a spring-mounted sliding element on the inner circumferential side of the housing 114 and one such element on the exterior of the housing 113, in each case in the region of the circumferential groove, can serve to ensure that the corresponding circumferential grooves and/or channel-like recesses are covered prior to the connection of the two housings. The sliding elements are to be spring-loaded and retractable such that, during joining of the two housings, the respective circumferential grooves or recesses are uncovered.

In the case of the configuration of FIG. 17, the channel-like recesses 117, 118 and/or the circumferential groove 116 form the auxiliary flushing channel 115".

The described variants enable the auxiliary sheath 104 to be permanently connected to the introducer sheath 101 and left connected thereto, and allow the two to be flushed together such that in the region of the sheath, bacteria are reliably prevented from penetrating into the body of the patient.

FIG. 18 shows an embodiment of the sheath assembly in which a sterile tube 130 is attached in a fluid-tight connection to an introducer sheath 101. In principle, said tube can be flushed from the introducer sheath 101 or from an auxiliary sheath 104' (shown only partially and schematically in FIG. 18).

The sterile tube 130 is itself embodied as fluid-tight and as a corrugated tube. It can be connected by means of a flange connection or adhesive connection 131, or generally by means of one of the connection types shown in FIGS. 13a to 13i, to the housing of the introducer sheath 114 and/or to the housing of the auxiliary sheath and/or to a catheter grip, and at least partially encompasses an auxiliary sheath, which is inserted partially into the introducer sheath. The sterile tube can also be clamped proximally directly to the catheter shaft.

Once a catheter has been inserted into the body of a patient, the auxiliary sheath as a whole can be received inside the sterile tube 130. A proximal end piece 132 has a through channel for the catheter, which is fed through said channel forming a seal.

Following the insertion process, the sterile tube can be axially compressed, and the end piece 132 can be connected to a flange 131, for example. The auxiliary sheath can also be torn away as a peel-away sheath, and pulled out of the introducer sheath into the sterile tube, where it will remain. The introducer sheath can then be sealed in relation to the sterile tube.

FIG. 19a shows an axial sectional view of a sheath assembly, in which a cord-shaped element/catheter 105 extends through the tubular part of an auxiliary sheath 21, which is in turn located inside the tubular section of the introducer sheath 41a. The cord-shaped element/catheter 105, which in the example is shown as a hollow catheter, has an outer diameter $d_1$. The tubular part of the auxiliary sheath 21 has an outer diameter $d_2$ and an inner diameter, which corresponds to the outer diameter $d_1$ of the cord-shaped element/catheter 105. The tubular part of the introducer sheath 41a has an inner diameter which corresponds to the outer diameter $d_2$ of the tubular part of the auxiliary sheath, and an outer diameter $d_{3a}$. In general, the wall thicknesses of the respective components cannot be randomly decreased on the basis of the material properties.

It is clear that, with a sheath assembly of this type, the outer diameter $d_{3a}$ of the system as a whole is relatively large due to the arrangement of the tubular sections of auxiliary sheath and introducer sheath one around the other, and at the point of passage through the skin of the patient results in a correspondingly high degree of trauma and risk of bleeding.

FIG. 19b shows an axial sectional view of a sheath assembly in which a cord-shaped element/catheter 105 extends through the tubular part of an auxiliary sheath 21, which in turn is located axially proximally to the tubular section of the introducer sheath, which therefore is not shown here.

It is clear that the outer diameter of the system in this region corresponds to the outer diameter $d_2$ of the tubular part of the auxiliary sheath.

FIG. 19c shows a further axially sectional view of the sheath assembly of FIG. 19b, which is located distally to the sectional view of FIG. 19b in a plane in which the cord-shaped element/catheter 105 extends through the tubular part of the introducer sheath 41a. A tubular part of the auxiliary sheath is not provided in this plane. Due to the absence of the auxiliary sheath in this section, the outer diameter $d_{3b}$ of the tubular section of the introducer sheath 41a can be designed as substantially smaller, for example, it can correspond to the outer diameter of the tubular section of the auxiliary sheath 21 or can be even smaller than this.

It is clear that with such a sheath assembly, the outer diameter $d_{3b}$ of the system as a whole is substantially smaller due to the positioning of the tubular sections of auxiliary sheath and introducer sheath one in front of the other axially, and results in correspondingly less trauma and risk of bleeding at the point of passage through the skin of the patient.

The invention claimed is:

1. A sheath assembly for insertion of a catheter into the body of a patient, said assembly comprising:
   an introducer sheath having a proximal end and a distal end, the distal end of the introducer sheath configured to be inserted into the body of a patient while the proximal end protrudes from the body of the patient;
   an introducer sheath housing coupled to the proximal end of the introducer sheath;
   an auxiliary sheath having a proximal end and a distal end, the distal end of the auxiliary sheath configured to be inserted into the introducer sheath housing;
   an auxiliary sheath housing coupled to the proximal end of the auxiliary sheath, comprising:
      first fastening means sized and positioned to detachably fasten the auxiliary sheath housing with respect to the introducer sheath housing when the distal end of the auxiliary sheath is proximal of a proximal end of the introducer sheath, and
      second fastening means sized and positioned to detachably fasten the catheter with respect to the auxiliary sheath.

2. The sheath assembly of claim 1, further comprising:
   a mechanical stop having a first contact surface and a second contact surface, the first contact surface being configured to prevent the distal end of the auxiliary sheath from moving distally past the mechanical stop, and the second contact surface being configured to prevent the proximal end of the introducer sheath from moving proximally past the mechanical stop, and
   wherein the first fastening means is further sized and positioned to detachably fasten the auxiliary sheath housing with respect to the introducer sheath housing when the distal end of the auxiliary sheath is in contact with the first contact surface of the mechanical stop and the proximal end of the introducer sheath is in contact with the second contact surface of the mechanical stop.

3. The sheath assembly of claim 1, further comprising:
   the auxiliary sheath further comprising:
      a tubular portion with an inner diameter and an outer diameter; and
   the introducer sheath further comprising:
      a tubular portion with an inner diameter and an outer diameter.

4. The sheath assembly of claim 3, wherein the first fastening means is further sized and positioned to detachably fasten the auxiliary sheath housing with respect to the introducer sheath housing when the tubular portion of the auxiliary sheath is proximal to the tubular portion of the introducer sheath.

5. The sheath assembly of claim 4, wherein the auxiliary sheath and the introducer sheath are configured to allow the catheter to extend through the tubular portion of the auxiliary sheath and through the tubular portion of the introducer sheath.

6. The sheath assembly of claim 5, wherein the outer diameter of the tubular portion of the auxiliary sheath is substantially the same as the outer diameter of the tubular portion of the introducer sheath.

7. The sheath assembly of claim 5, wherein the outer diameter of the tubular portion of the auxiliary sheath is larger than the outer diameter of the tubular portion of the introducer sheath housing.

8. The sheath assembly of claim 4, wherein the inner diameter of the tubular portion of the introducer sheath is substantially the same as an outer diameter of the catheter.

9. The sheath assembly claim 4, wherein the inner diameter of the tubular portion of the auxiliary sheath is substantially the same as an outer diameter of the catheter.

10. The sheath assembly of claim 4, wherein the tubular portion of the introducer sheath is configured to be inserted into the body of the patient.

* * * * *

UNITED STATES PATENT AND TRADEMARK OFFICE
CERTIFICATE OF CORRECTION

PATENT NO. : 10,881,836 B2
APPLICATION NO. : 16/122517
DATED : January 5, 2021
INVENTOR(S) : Joerg Schumacher et al.

Page 1 of 1

It is certified that error appears in the above-identified patent and that said Letters Patent is hereby corrected as shown below:

In the Specification

Column 12, Line 23 - Delete "explanation" and insert --explantation-- therefor.

Column 18, Line 30 - Delete "13$a$ to 13$j$." and insert --13$a$ to 13$i$.-- therefor.

Column 20, Line 8 - Delete "114" and insert --101-- therefor.

In the Claims

Column 22, Line 34 - In Claim 9, after "assembly", insert --of--.

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*